(12) United States Patent
Shinde et al.

(10) Patent No.: US 9,200,236 B2
(45) Date of Patent: *Dec. 1, 2015

(54) OMEGA 7 RICH COMPOSITIONS AND METHODS OF ISOLATING OMEGA 7 FATTY ACIDS

(71) Applicant: Heliae Development, LLC, Gilbert, AZ (US)

(72) Inventors: Sandip Shinde, Chandler, AZ (US); Aniket Kale, Chandler, AZ (US); Tom Kulaga, Chandler, AZ (US); Jason D. Licamele, Scottsdale, AZ (US); Anna Lee Tonkovich, Gilbert, AZ (US)

(73) Assignee: HELIAE DEVELOPMENT, LLC, Gilbert, AZ (US)

( * ) Notice: Subject to any disclaimer, the term of this patent is extended or adjusted under 35 U.S.C. 154(b) by 54 days.

This patent is subject to a terminal disclaimer.

(21) Appl. No.: 13/680,961

(22) Filed: Nov. 19, 2012

(65) Prior Publication Data

US 2013/0129775 A1     May 23, 2013

Related U.S. Application Data

(60) Provisional application No. 61/561,145, filed on Nov. 17, 2011, provisional application No. 61/610,160, filed on Mar. 13, 2012.

(51) Int. Cl.

| | | |
|---|---|---|
| *A61K 8/36* | (2006.01) |
| *A61K 8/97* | (2006.01) |
| *C11B 3/00* | (2006.01) |
| *C07C 1/22* | (2006.01) |
| *C12P 7/64* | (2006.01) |
| *C12N 1/12* | (2006.01) |
| *A23D 9/00* | (2006.01) |
| *A23D 9/02* | (2006.01) |
| *A23K 1/16* | (2006.01) |
| *C11B 1/10* | (2006.01) |
| *C11B 3/12* | (2006.01) |
| *C11B 7/00* | (2006.01) |
| *C11C 3/02* | (2006.01) |
| *A23L 1/30* | (2006.01) |
| *C11C 3/00* | (2006.01) |
| *C10L 1/02* | (2006.01) |
| *A61Q 19/00* | (2006.01) |

(52) U.S. Cl.
CPC . *C11B 3/001* (2013.01); *A23D 9/00* (2013.01); *A23D 9/02* (2013.01); *A23K 1/164* (2013.01); *A23L 1/3008* (2013.01); *A61K 8/361* (2013.01); *A61K 8/975* (2013.01); *A61Q 19/00* (2013.01); *C07C 1/22* (2013.01); *C10L 1/026* (2013.01); *C11B 1/10* (2013.01); *C11B 3/006* (2013.01); *C11B 3/12* (2013.01); *C11B 7/00* (2013.01); *C11C 3/00* (2013.01); *C11C 3/003* (2013.01); *C11C 3/02* (2013.01); *C12N 1/12* (2013.01); *C12P 7/6409* (2013.01); *C10G 2300/1014* (2013.01); *Y02E 50/13* (2013.01)

(58) Field of Classification Search
CPC . A61K 47/10; A61K 2300/00; A61K 31/202; A61K 9/0014; A61K 47/44; A61K 36/02; A61K 8/92
See application file for complete search history.

(56) References Cited

U.S. PATENT DOCUMENTS

| | | |
|---|---|---|
| 3,258,467 A | 6/1966 | Anderson |
| 4,062,882 A | 12/1977 | Sen Gupta |
| 4,190,538 A | 2/1980 | Chen |
| 4,264,452 A | 4/1981 | Chen |
| 4,267,038 A | 5/1981 | Thompson |
| 4,341,038 A | 7/1982 | Bloch |
| 4,736,756 A | 4/1988 | Grollier |
| 4,749,565 A | 6/1988 | Grollier |
| 4,787,981 A | 11/1988 | Tanahashi |
| 4,795,638 A | 1/1989 | Ayache et al. |
| 4,851,339 A | 7/1989 | Hills |
| 4,925,557 A | 5/1990 | Ahlberg |
| 5,079,227 A | 1/1992 | Handjani et al. |
| 5,130,242 A | 7/1992 | Barclay |
| 5,171,577 A | 12/1992 | Griat et al. |
| 5,179,012 A | 1/1993 | Gudin |
| 5,190,936 A | 3/1993 | Laugier et al. |
| 5,338,673 A | 8/1994 | Thepenier |

(Continued)

FOREIGN PATENT DOCUMENTS

| | | |
|---|---|---|
| CA | 2249103 A1 | 4/1999 |
| EP | 1057833 | 12/2000 |

(Continued)

OTHER PUBLICATIONS

Wang et al., Protein Theory and Technology, Archival Library of Chinese Publications CIP Data, 2004, No. 122609, Science Press, ISBN-7-03-014646-8, 10 pages.
United States Environmental Protection Agency, "Membrane Filtration Guidance Manual," Jun. 2003, Chapter p. 2-15, 5 pages.
Samarasinghe et al., "Algal cell rupture using high pressure homogenization as a prelude to oil extraction," Renewable Energy, 48, 2012, pp. 300-308.
Grima et al., "Gram-scale purification of eicosapentaenoic acid (EPA, 20:5n-3) from wet Phaeodactylum tricornutum UTEX 640 biomass," Journal of Applied Phycology, 8, 1996, pp. 359-367.

(Continued)

*Primary Examiner* — Terry A McKelvey
*Assistant Examiner* — Catheryne Chen
(74) *Attorney, Agent, or Firm* — Wilmer Cutler Pickering Hale and Dorr LLP

(57) ABSTRACT

Disclosed here are compositions rich in omega-7 fatty acids, including palmitoleic acid, and products rich in omega-7 fatty acids derived from algal biomass. The algae and/or compositions rich in omega-7 fatty acids may be used in products or as ingredients of products. Methods and systems for increasing the production or concentration of omega-7 fatty acids, and isolating omega-7 fatty acids from algal biomass are also disclosed herein.

11 Claims, 8 Drawing Sheets

(56) References Cited

U.S. PATENT DOCUMENTS

| | | |
|---|---|---|
| 5,374,657 A | 12/1994 | Kyle |
| 5,440,028 A | 8/1995 | Buchholz |
| 5,539,133 A | 7/1996 | Kohn |
| 5,545,329 A | 8/1996 | LaMonica |
| 5,618,521 A | 4/1997 | De Rigal et al. |
| 5,658,575 A | 8/1997 | Ribier et al. |
| 5,658,767 A | 8/1997 | Kyle |
| 5,744,305 A | 4/1998 | Fodor |
| 5,837,832 A | 11/1998 | Chee |
| 5,874,092 A | 2/1999 | Roulier et al. |
| 5,910,254 A | 6/1999 | Guelcher |
| 5,925,364 A | 7/1999 | Ribier et al. |
| 6,036,968 A | 3/2000 | Roulier et al. |
| 6,045,814 A | 4/2000 | Roulier et al. |
| 6,066,328 A | 5/2000 | Ribier et al. |
| 6,162,458 A | 12/2000 | Asada et al. |
| 6,166,091 A | 12/2000 | Kojima |
| 6,166,231 A | 12/2000 | Hoeksema |
| 6,180,122 B1 | 1/2001 | Roulier et al. |
| 6,214,574 B1 | 4/2001 | Kopf |
| 6,261,579 B1 | 7/2001 | Roulier et al. |
| 6,280,765 B1 | 8/2001 | Gueret |
| 6,284,257 B1 | 9/2001 | Khayat et al. |
| 6,337,315 B1 | 1/2002 | Mahe et al. |
| 6,342,235 B1 | 1/2002 | Samain et al. |
| 6,344,186 B1 | 2/2002 | Hansenne et al. |
| 6,346,256 B1 | 2/2002 | Simon |
| 6,372,460 B1 | 4/2002 | Gladue |
| 6,379,401 B1 | 4/2002 | Legrand et al. |
| 6,416,768 B1 | 7/2002 | Ravaux et al. |
| 6,419,935 B1 | 7/2002 | Gueret |
| 6,441,208 B2 | 8/2002 | Bijl |
| 6,461,662 B2 | 10/2002 | Cain et al. |
| 6,495,140 B1 | 12/2002 | Collins |
| 6,503,520 B1 | 1/2003 | Afriat |
| 6,506,391 B1 | 1/2003 | Biatry |
| 6,524,486 B2 | 2/2003 | Borodyanski |
| 6,579,714 B1 | 6/2003 | Hirabayashi |
| 6,623,751 B2 | 9/2003 | Gueret |
| 6,630,131 B2 | 10/2003 | Chevalier et al. |
| 6,689,345 B2 | 2/2004 | Jager Lezer |
| 6,727,373 B2 | 4/2004 | Bijl |
| 6,750,048 B2 | 6/2004 | Ruecker |
| 6,783,792 B2 | 8/2004 | McDaniel, III et al. |
| 6,812,192 B2 | 11/2004 | Ribery et al. |
| 6,818,239 B2 | 11/2004 | Kagan |
| 6,906,106 B2 | 6/2005 | Chevalier |
| 6,994,846 B2 | 2/2006 | L'Alloret |
| 7,015,014 B2 | 3/2006 | Schaap |
| 7,040,827 B2 | 5/2006 | Gueret |
| 7,115,760 B2 | 10/2006 | Sparso et al. |
| 7,148,366 B2 | 12/2006 | Cheryan |
| 7,234,885 B2 | 6/2007 | Gueret |
| 7,258,852 B2 | 8/2007 | Maubru |
| 7,282,067 B2 | 10/2007 | Burgaud et al. |
| 7,381,403 B2 | 6/2008 | Simonnet |
| 7,396,548 B2 | 7/2008 | Kyle |
| 7,410,636 B2 | 8/2008 | Collin |
| 7,575,768 B2 | 8/2009 | Perlman |
| 7,608,270 B2 | 10/2009 | Beckett |
| 7,655,833 B2 | 2/2010 | Heilmann et al. |
| 7,678,931 B2 | 3/2010 | Fichtali |
| 7,695,626 B2 | 4/2010 | Dueppen |
| 7,714,185 B2 | 5/2010 | Napier et al. |
| 7,757,866 B2 | 7/2010 | McCutchen |
| 7,763,587 B2 | 7/2010 | Michelet et al. |
| 7,795,230 B2 | 9/2010 | Michelet et al. |
| 7,816,570 B2 | 10/2010 | Roberts |
| 7,857,865 B2 | 12/2010 | Guerin et al. |
| 7,857,866 B2 | 12/2010 | Guerin |
| 7,868,195 B2 | 1/2011 | Fleischer |
| 7,883,882 B2 | 2/2011 | Franklin |
| 7,888,540 B2 | 2/2011 | Deluga |
| 7,923,223 B2 | 4/2011 | Seip et al. |
| 7,943,792 B2 | 5/2011 | Berry |
| 7,977,318 B2 | 7/2011 | Michelet et al. |
| 8,048,426 B2 | 11/2011 | Hsieh et al. |
| 8,062,688 B2 | 11/2011 | Greither |
| 8,084,038 B2 | 12/2011 | Kale |
| 8,115,022 B2 | 2/2012 | Kale |
| 8,137,555 B2 | 3/2012 | Kale |
| 8,137,556 B2 | 3/2012 | Kale |
| 8,137,558 B2 | 3/2012 | Kale |
| 8,142,659 B2 | 3/2012 | Kale |
| 8,152,870 B2 | 4/2012 | Kale |
| 8,153,137 B2 | 4/2012 | Kale |
| 8,182,556 B2 | 5/2012 | Kale |
| 8,182,689 B2 | 5/2012 | Kale |
| 8,187,463 B2 | 5/2012 | Kale |
| D661,164 S | 6/2012 | Licamele |
| 8,197,691 B2 | 6/2012 | Kale |
| 8,202,425 B2 | 6/2012 | Kale |
| 8,211,308 B2 | 7/2012 | Kale |
| 8,211,309 B2 | 7/2012 | Kale |
| 8,218,018 B2 | 7/2012 | Washisu |
| 8,242,296 B2 | 8/2012 | Kale |
| 8,273,248 B1 | 9/2012 | Kale |
| 8,293,108 B1 | 10/2012 | Kale |
| 8,308,948 B2 | 11/2012 | Kale |
| 8,308,949 B1 | 11/2012 | Kale |
| 8,308,950 B2 | 11/2012 | Kale |
| 8,308,951 B1 | 11/2012 | Kale |
| 8,313,647 B2 | 11/2012 | Kale |
| 8,313,648 B2 | 11/2012 | Kale |
| 8,318,018 B2 | 11/2012 | Kale |
| 8,318,019 B2 | 11/2012 | Kale |
| 8,323,501 B2 | 12/2012 | Kale |
| 8,329,036 B2 | 12/2012 | Kale |
| 8,341,877 B2 | 1/2013 | Licamele |
| 8,365,462 B2 | 2/2013 | Licamele |
| 8,382,986 B2 | 2/2013 | Kale |
| 8,383,845 B2 | 2/2013 | Catchpole et al. |
| 8,475,660 B2 | 7/2013 | Kale |
| 8,476,412 B2 | 7/2013 | Kale |
| 8,513,383 B2 | 8/2013 | Kale |
| 8,513,384 B2 | 8/2013 | Kale |
| 8,513,385 B2 | 8/2013 | Kale |
| 8,551,336 B2 | 10/2013 | Kale |
| 8,552,160 B2 | 10/2013 | Kale |
| 8,552,560 B2 | 10/2013 | Bhatt |
| 8,574,587 B2 | 11/2013 | Kale |
| 2001/0007671 A1 | 7/2001 | Gueret |
| 2001/0036466 A1 | 11/2001 | Roulier et al. |
| 2002/0009493 A1 | 1/2002 | Schwendeman |
| 2002/0025333 A1 | 2/2002 | Agostini et al. |
| 2002/0028222 A1 | 3/2002 | Afriat |
| 2002/0034526 A1 | 3/2002 | Agostini et al. |
| 2002/0034528 A1 | 3/2002 | Agostini et al. |
| 2002/0131948 A1 | 9/2002 | Toumi et al. |
| 2002/0187174 A1 | 12/2002 | Biatry |
| 2002/0197289 A1 | 12/2002 | Chevalier et al. |
| 2003/0017558 A1 | 1/2003 | Pham et al. |
| 2003/0024556 A1 | 2/2003 | Guiramand et al. |
| 2003/0054070 A1 | 3/2003 | Bridges |
| 2003/0059391 A1 | 3/2003 | L'Alloret |
| 2003/0059392 A1 | 3/2003 | L'Alloret |
| 2003/0072732 A1 | 4/2003 | Breton et al. |
| 2003/0108497 A1 | 6/2003 | Chevalier et al. |
| 2003/0129157 A1 | 7/2003 | Sonneville-Aubrun et al. |
| 2003/0224077 A1 | 12/2003 | Mahe et al. |
| 2004/0013622 A1 | 1/2004 | Godbout |
| 2004/0131580 A1 | 7/2004 | Hagino |
| 2004/0137023 A1 | 7/2004 | Dalko et al. |
| 2004/0175338 A1 | 9/2004 | Filippi et al. |
| 2004/0223935 A1 | 11/2004 | Meunier |
| 2004/0258644 A1 | 12/2004 | Simonnet |
| 2005/0026795 A1 | 2/2005 | Filippi |
| 2005/0135104 A1 | 6/2005 | Crabb |
| 2005/0164192 A1 | 7/2005 | Graham |
| 2005/0170479 A1 | 8/2005 | Weaver |
| 2005/0191337 A1 | 9/2005 | Gueret |
| 2006/0039936 A1 | 2/2006 | Fares et al. |
| 2006/0057085 A1 | 3/2006 | Lezer |
| 2006/0088574 A1 | 4/2006 | Manning et al. |

(56) References Cited

U.S. PATENT DOCUMENTS

| | | |
|---|---|---|
| 2006/0122410 A1 | 6/2006 | Fichtali |
| 2006/0141078 A1 | 6/2006 | Guillou et al. |
| 2006/0147400 A1 | 7/2006 | Piot |
| 2006/0165630 A1 | 7/2006 | Rubinstenn et al. |
| 2006/0280840 A1 | 12/2006 | Robertson |
| 2007/0025937 A1 | 2/2007 | Fares et al. |
| 2007/0025976 A1 | 2/2007 | Kluetz |
| 2007/0098840 A1 | 5/2007 | Axelrod |
| 2007/0122493 A1 | 5/2007 | Funayama |
| 2007/0131579 A1 | 6/2007 | Koivusalmi |
| 2007/0190001 A1 | 8/2007 | Jacques et al. |
| 2007/0196383 A1 | 8/2007 | Murakami |
| 2007/0196893 A1 | 8/2007 | Weiss |
| 2007/0264271 A1 | 11/2007 | ElSohly |
| 2008/0008670 A1 | 1/2008 | Arnaud et al. |
| 2008/0014162 A1 | 1/2008 | Willemin et al. |
| 2008/0019933 A1 | 1/2008 | Thevenet et al. |
| 2008/0038290 A1 | 2/2008 | Renimel |
| 2008/0044373 A1 | 2/2008 | Ilekti et al. |
| 2008/0069786 A1 | 3/2008 | Rodriguez et al. |
| 2008/0118964 A1 | 5/2008 | Huntley |
| 2008/0119527 A1 | 5/2008 | Baldo |
| 2008/0138368 A1 | 6/2008 | Lezer |
| 2008/0152607 A1 | 6/2008 | Malle et al. |
| 2008/0155888 A1 | 7/2008 | Vick |
| 2008/0159970 A1 | 7/2008 | Willemin |
| 2008/0160593 A1 | 7/2008 | Oyler |
| 2008/0163543 A1 | 7/2008 | Abhari |
| 2008/0171791 A1 | 7/2008 | Ordman |
| 2008/0176304 A1 | 7/2008 | Lee |
| 2008/0199489 A1 | 8/2008 | Parrinello |
| 2008/0220515 A1 | 9/2008 | McCall |
| 2008/0254077 A1 | 10/2008 | Prigent |
| 2008/0274203 A1 | 11/2008 | Bruheim |
| 2008/0293132 A1 | 11/2008 | Goldman |
| 2009/0028807 A1 | 1/2009 | Giustiniani et al. |
| 2009/0029445 A1 | 1/2009 | Eckelberry |
| 2009/0041815 A1 | 2/2009 | Legendre |
| 2009/0049739 A1 | 2/2009 | Morgan |
| 2009/0056201 A1 | 3/2009 | Morgan |
| 2009/0071064 A1 | 3/2009 | Machacek |
| 2009/0111876 A1 | 4/2009 | Hsieh |
| 2009/0148918 A1 | 6/2009 | Trimbur |
| 2009/0148931 A1 | 6/2009 | Wilkerson |
| 2009/0162919 A1 | 6/2009 | Radaelli |
| 2009/0170801 A1 | 7/2009 | Hao |
| 2009/0181438 A1 | 7/2009 | Sayre |
| 2009/0181463 A1 | 7/2009 | Chen |
| 2009/0203116 A1 | 8/2009 | Bazaire |
| 2009/0215140 A1 | 8/2009 | Kurano |
| 2009/0221677 A1 | 9/2009 | Ntambi et al. |
| 2009/0232785 A1 | 9/2009 | Breton et al. |
| 2009/0234146 A1 | 9/2009 | Cooney |
| 2010/0047201 A1 | 2/2010 | Lalleman et al. |
| 2010/0047295 A1 | 2/2010 | Giagnorio |
| 2010/0050502 A1 | 3/2010 | Wu |
| 2010/0055741 A1 | 3/2010 | Galvez |
| 2010/0068772 A1 | 3/2010 | Downey |
| 2010/0077654 A1 | 4/2010 | Wu |
| 2010/0081835 A1 | 4/2010 | Wu |
| 2010/0093047 A1 | 4/2010 | Newman |
| 2010/0120104 A1 | 5/2010 | Reed |
| 2010/0130389 A1 | 5/2010 | Lightford |
| 2010/0151112 A1 | 6/2010 | Franklin |
| 2010/0170144 A1 | 7/2010 | Day |
| 2010/0196971 A1 | 8/2010 | Lin |
| 2010/0221200 A1 | 9/2010 | During |
| 2010/0233761 A1 | 9/2010 | Czartoski |
| 2010/0239712 A1 | 9/2010 | Brooks |
| 2010/0255541 A1 | 10/2010 | Hu |
| 2010/0261922 A1 | 10/2010 | Fleischer |
| 2010/0267126 A1 | 10/2010 | Jacobs |
| 2010/0291007 A1 | 11/2010 | Mahe et al. |
| 2010/0297331 A1 | 11/2010 | Brooks |
| 2010/0297749 A1 | 11/2010 | Aravanis |
| 2010/0303990 A1 | 12/2010 | Brooks |
| 2010/0311156 A1 | 12/2010 | Beliaev |
| 2010/0317088 A1 | 12/2010 | Radaelli |
| 2010/0323436 A1 | 12/2010 | Lee |
| 2010/0331429 A1 | 12/2010 | Lorant |
| 2010/0331586 A1 | 12/2010 | Hanks |
| 2011/0003331 A1 | 1/2011 | Pavia |
| 2011/0070632 A1 | 3/2011 | Katoch |
| 2011/0086386 A1 | 4/2011 | Czartoski |
| 2011/0124034 A1 | 5/2011 | Kuehnle |
| 2011/0138682 A1 | 6/2011 | Demaris |
| 2011/0143012 A1 | 6/2011 | Rettenmaier |
| 2011/0171153 A1 | 7/2011 | Desenne et al. |
| 2011/0174734 A1 | 7/2011 | Seibert |
| 2011/0182930 A1 | 7/2011 | Erlanson-Albertsson |
| 2011/0195484 A1 | 8/2011 | Kale |
| 2011/0197496 A1 | 8/2011 | O'Connor |
| 2011/0203168 A1 | 8/2011 | Franklin et al. |
| 2011/0207820 A1 | 8/2011 | Cattolico |
| 2011/0252696 A1 | 10/2011 | Franklin |
| 2011/0258926 A1 | 10/2011 | Bijl |
| 2011/0262505 A1 | 10/2011 | Athwal |
| 2011/0294196 A1 | 12/2011 | Machin |
| 2012/0021091 A1 | 1/2012 | Kale |
| 2012/0021457 A1 | 1/2012 | Tang |
| 2012/0029170 A1 | 2/2012 | Kale |
| 2012/0035348 A1 | 2/2012 | Kale |
| 2012/0046477 A1 | 2/2012 | Kale |
| 2012/0053323 A1 | 3/2012 | Kale |
| 2012/0053324 A1 | 3/2012 | Kale |
| 2012/0064508 A1 | 3/2012 | Licamele |
| 2012/0065378 A1 | 3/2012 | Kale |
| 2012/0101258 A1 | 4/2012 | Kale |
| 2012/0108793 A1 | 5/2012 | Kale |
| 2012/0119862 A1 | 5/2012 | Franklin |
| 2012/0122164 A1 | 5/2012 | El-Shafie |
| 2012/0130099 A1 | 5/2012 | Wittenberg |
| 2012/0135478 A1 | 5/2012 | Hu |
| 2012/0135479 A1 | 5/2012 | Dillon |
| 2012/0137574 A1 | 6/2012 | Stephen |
| 2012/0157734 A1 | 6/2012 | Strege |
| 2012/0164701 A1 | 6/2012 | Trimbur |
| 2012/0225941 A1 | 9/2012 | Green |
| 2012/0264957 A1 | 10/2012 | Kale |
| 2013/0129775 A1 | 5/2013 | Shinde |
| 2013/0167432 A1 | 7/2013 | Kale |
| 2013/0217904 A1 | 8/2013 | Kale |
| 2014/0005422 A1 | 1/2014 | Kale |

FOREIGN PATENT DOCUMENTS

| | | |
|---|---|---|
| EP | 1166770 B1 | 9/2002 |
| EP | 0933077 B1 | 2/2003 |
| EP | 1299003 | 4/2003 |
| EP | 1820499 A1 | 8/2007 |
| EP | 1876906 | 1/2008 |
| EP | 1920777 A1 | 5/2008 |
| EP | 2030626 A1 | 3/2009 |
| EP | 1343454 B1 | 12/2009 |
| EP | 2272383 A1 | 1/2011 |
| EP | 2272383 A1 | 1/2011 |
| JP | 6022772 A | 2/1994 |
| JP | 2002220402 A | 8/2002 |
| WO | 9112730 A2 | 9/1991 |
| WO | WO-92/12711 | 8/1992 |
| WO | WO-94/02166 | 2/1994 |
| WO | 0146133 A1 | 6/2001 |
| WO | WO-02/49602 | 6/2002 |
| WO | 2004019694 | 3/2004 |
| WO | 2005120174 A2 | 12/2005 |
| WO | 2006046943 A2 | 5/2006 |
| WO | 2006095964 A1 | 9/2006 |
| WO | 2008031092 A2 | 3/2008 |
| WO | 2008031092 A3 | 3/2008 |
| WO | WO-2008/034699 | 3/2008 |
| WO | 2008060571 A2 | 5/2008 |
| WO | WO-2008/074654 | 6/2008 |
| WO | 2008144583 A1 | 11/2008 |
| WO | 2009082696 A1 | 7/2009 |

(56) References Cited

FOREIGN PATENT DOCUMENTS

| WO | WO-2009/105620 | 8/2009 |
|---|---|---|
| WO | 2009158658 A2 | 12/2009 |
| WO | 2010036334 A1 | 4/2010 |
| WO | 2010039030 A1 | 4/2010 |
| WO | WO-2010/063032 | 6/2010 |
| WO | 2010085853 A1 | 8/2010 |
| WO | 2010089063 A1 | 8/2010 |
| WO | WO-2010/088001 | 8/2010 |
| WO | 2010104444 A1 | 9/2010 |
| WO | 2010104922 A1 | 9/2010 |
| WO | 2010115996 A1 | 10/2010 |
| WO | 2010120939 A2 | 10/2010 |
| WO | 2010123903 A1 | 10/2010 |
| WO | 2010132413 A1 | 11/2010 |
| WO | 2010132414 A1 | 11/2010 |
| WO | 2010138620 A1 | 12/2010 |
| WO | 2010151606 A1 | 12/2010 |
| WO | WO-2010/149662 | 12/2010 |
| WO | WO-2010/150262 | 12/2010 |
| WO | 2011003024 A2 | 1/2011 |
| WO | 2011027301 A1 | 3/2011 |
| WO | 2011057406 A1 | 5/2011 |
| WO | 2011069372 A1 | 6/2011 |
| WO | WO-2011/067666 | 6/2011 |
| WO | 2011107977 A1 | 9/2011 |
| WO | 2011127127 A2 | 10/2011 |
| WO | 2011127157 A1 | 10/2011 |
| WO | 2011127160 A1 | 10/2011 |
| WO | 2011127161 A1 | 10/2011 |
| WO | 2011127165 A2 | 10/2011 |
| WO | 2011127167 A1 | 10/2011 |
| WO | 2011127169 A1 | 10/2011 |
| WO | 2011127171 A1 | 10/2011 |
| WO | 2011127172 A1 | 10/2011 |
| WO | 2012024340 A2 | 2/2012 |
| WO | 2012062962 A1 | 5/2012 |
| WO | 2012138380 | 10/2012 |
| WO | 2012138381 | 10/2012 |
| WO | 2012138382 | 10/2012 |
| WO | 2012138438 A1 | 10/2012 |
| WO | 2013075116 | 5/2013 |
| WO | 2013142687 | 9/2013 |
| WO | 2013142694 | 9/2013 |

OTHER PUBLICATIONS

Chen et al., "Review of the biological and engineering aspects of algae to fuels approach," Int J Agric & Biol Eng, vol. 2, No. 4, Dec. 2009, 30 pages.
Nicholson et al., "Determination and Significance of Emerging Algal Toxins (Cyanotoxins)," Awwa Research Foundation and Cooperative Research Centre for Water Quality and Treatment, Jul. 2007, pp. 14-15, 5 pages, IBSN-10: 1583215630, ISBN-13: 978-1583215364.
Alamu et al., "Effect of Ethanol-palm Kernel Oil Ratio on Alkali-catalyzed Biodiesel Yield," Fuel, 87, 2008, pp. 1529-1533.
Andres et al., "Evaluation of Marine Microalga Nannochloropsis sp. As a Potential Dietary Supplement. Chemical, Nutritional and Short Term Toxicological Evaluation in Rats," Nutrition Research, vol. 12, Issue No. 10, Oct. 1992, pp. 1273-1284, Abstract Only, 1 page.
Author Unknown, "If a Goddess Wore Makeup," 4 pages, retrieved from http://ifagoddessworemakeup.com/ingredients on Apr. 23, 2012.
Author Unknown, "Best Face Wash for Men," 3 pages, retrieved from http://jagged81.hubpages.com/hub/Best-Face-Wash-for-Men on Apr. 19, 2012.
Author Unknown, "Supercritical Omega 7, Skin and Hair Secret of the Ancients*," retrieved from http://www.newchapter.com/targeted-herbal-formulas/supercritical-omega-7 on Aug. 23, 2012, 2 pages.
Author Unknown, "SIBU Omega-7 Chocolates," retrieved from http://www.sibubeauty.com/sibu_omega-7_chocolates.php on Aug. 23, 2012, 1 page.
Author Unknown, "GenEssentials Super Fruit Oil," retrieved from http://superfoods.genesistoday.com/products/supplements/genes-sentials-super-fruit-oil on Apr. 19, 2012, 2 pages.
Author Unknown, "Omega-7 EFA5," retrieved from http://www.swansonvitamins.com/omega-7-efas on Aug. 23, 2012, 2 pages.
Author Unknown, "Vitacost Sea Buckthorn Oil (Omega-7)—450 mg—30 L," retrieved from http://www.vitacost.com/vitacost-sea-buckthorn-oil-omega-7-450-mg-30-liquid-capsules on Aug. 23, 2012, 3 pages.
Author Unknown, "Benefits of Botanicals," retrieved from http://www.benefitsofbotanicals.com/Skin-Care.html on Apr. 19, 2012, 5 pages.
Author Unknown, "In-Room Bath Menu," retrieved from http://www.jumeirah.com/en/hotels-and-resorts/destinations/dubai/jumeirah-emirates-towe on Apr. 19, 2012, 1 page.
Author Unknown, "No Vejez Night & Day Cream," retrieved from http://www.maxvite.com/284/6502/No_Velez-product.html on Apr. 23, 2012, 2 pages.
Author Unknown,"Macadamia Deep Repair Masque," retrieved from http://www.myhaircare.com/au/Deep_Repair_Masque_1173.html on Apr. 23, 2012, 6 pages.
Author Unknown, "Sea Buckthorn Oil Blend—Wicde Spectrum Support w/ Omega-7," retrieved from http://www.seabuckwonders.com/products/seabuckthorn_oil.html on Apr. 19, 2012, 1 page.
Author Unknown, "Agipal Technical Data Sheet, Chilean Hazelnut Virgin V.O. Gevuina avellana Mol," retrieved from www.aromaterra.hr/Tekstovi/pdf/Ulje_cileanskog_ljenjaka.pdf, Oct. 2005, 2 pages.
Author Unknown, "Spirulina Skincare UK—Distributors of Hofigal Products," retrieved from http://www.spirulinskincare.co.uk/hofigal_products.shtml on Apr. 19, 2012, 2 pages.
Aromtech, "Omega 7 Sea Buckthorn Oil Capsule for Women's Health," 23 pages, retrieved from www.herbapharma.it/OMEGA_7_Sea_Buckthorn_Oil_Capsule_for_Wo . . . , date unknown, 2004
Baoru et al., Effects of Dietary Supplementation of Seabuckthorn (Hippophae rhamnoides) Oils on Fatty Acids in Patients with Atopic Dermatitis, 2000, 5 pgs., retrieved from www.seabuckthorn.com/file.
Berthiaume et al., "Oleotek, Extraction, Characterisation and Valorisation into Value-Added Products of Residual Mink Fat," retrieved from www.oleotek.org/FichiersUpload/Softsystem/PosterJosee-070507-02-JLAT.pdf, date unknown, 1 page, 2011.
Bi et al., "Low-melting-point Biodiesel Derived from Corn Oil via Urea Complexation," Bioresource Technology, 101, 2010, pp. 1220-1226.
Braden et al., "Dietary Polyunsaturated Fat in Relation to Mammary Carcinogenesis in Rats," Lipids, Apr. 1986, vol. 21, Issue No. 4, pp. 285-288.
Carvalho et al., "Light Requirements in Microalgal Photobioreactors: an Overview of Biophotonic Aspects," Appl. Microbiol. Biotechnol., 2011, 89, pp. 1275-1288.
Connelly, et al., "Algae-Derived Omega-7 Accelerates Wound Healing," University of Texas at Austin, Center for Electromechanics and OpenAlgae LLC presentation, downloaded from www.utexas.edu, date unknown, 8 pages, 2011.
Crexi et al., "Polyunsaturated Fatty Acid Concentrates of Carp Oil: Chemical Hydrolysis and Urea Complexation," J. Am. Oil Chem. Soc., 2012, 89, pp. 329-334.
Curb et al., "Serum Lipid Effects of a High-Monounsaturated Fat Diet Based on Macadamia Nuts," Arch Intern Med/vol. 160, Apr. 2000, pp. 1154-1158, downloaded from http://archinte.jamanetwork.com on Oct. 15, 2013.
Doan et al., "Screening of Marine Microalgae for Biodiesel Feedstock," Biomass & Bioenergy, 35, 2011, pp. 2534-2544.
Encinar et al., "Biodiesel Fuels From Vegetable Oils: Transesterification of Cynara cardunculus L. Oils with Ethanol," Energy & Fuels, 2002, 16, pp. 443-450.
Fjerbaek et al., "A Review of the Current State of Biodiesel Production Using Enzymatic Transesterification," Biotechnology and Bioengineering, vol. 102, No. 5, Apr. 2009, pp. 1298-1315.
Gogus et al., "n-3 Omega Fatty Acids: A Review of Current Knowledge," International Journal of Food Science & Technology, 2010, 45, pp. 417-436.
Gutierrez et al., "Effects of Drying Method on the Extraction Yields and Quality of Oils from Quebec Sea Buckthorn (Hippophaë rhamnoides L.) Seeds and Pulp," Food Chemistry 106, 2008, pp. 896-904.

(56) References Cited

OTHER PUBLICATIONS

Haze et al., "2-Nonenal Newly Found in Human Body Odor Tends to Increase with Aging," The Journal of Investigative Dermatology, vol. 116, No. 4, Apr. 2001, pp. 520-524.
Henderson, "A Little Bit of Heaven From Omega-7, Digestive Health Support," The Doctor's Prescription for Healthy Living, vol. 9, No. 6, Oct. 2013, pp. 44-46.
Joseph, Fatty Acid Composition of Commercial Menhaden, Brevoortia spp., Oils, 1982 and 1983, Marine Fisheries Review, 47, 3, 1985, pp. 30-37.
Kaijser et al., "Oxidative Stability and Lipid Composition of Macadamia Nuts Grown in New Zealand," Food Chemistry, 71, 2000, pp. 67-70.
Kim, et al., "Ionic Liquid-mediated Extraction of Lipids from Algal Biomass," Bioresource Technology, 2011, doi: 10.1016/j.biortech.2011.04.064, 4 pages.
Koberg et al., "Bio-diesel Production Directly from the Microalgae Biomass of Nannochloropsis by Microwave and Ultrasound Radiation," Bioresource Technology, 102, 2011, pp. 4265-4269.
Krienitz et al., "The High Content of Polyunsaturated Fatty Acids in Nannochloropsis limnetica (Eustigmatophyceae) and its Implication for Food Web Interactions, Freshwater Aquaculture and Biotechnology," Limnologica, 36, 2006, pp. 204-210.
Li et al., "One-step Production of Biodiesel from Nannochloropsis sp. On Solid Base Mg—Zr Catalyst," Applied Energy, 88, 2011, pp. 3313-3317.
Liu et al., "Differential Lipid and Fatty Acid Profiles of Photoautotrophic and Heterotrophic Chlorella Zofingiensis: Assessment of Algal Oils for Biodiesel Production," Bioresour Technol., Jan. 2011, 102, 1, pp. 106-110, Abstract Only, 1 page, retrieved from http://www.ncbi.nlm.nih.gov/pubmed/20591657 on Aug. 27, 2012.
Liu et al., "Molasses-based Growth and Production of Oil and Astaxanthin by Chlorella Zofingiensis," Bioresour. Technol., Mar. 2012, 107, pp. 393-398, Abstract Only, 1 page, retrieved from http://www.ncbi.nlm.nih.gov/pubmed/22221991 on Aug. 27, 2012.
Liu, et al., "Transesterification of Soybean Oil to Biodiesel Using CaO as a Solid Base Catalyst," Fuel, 87, 2008, pp. 216-221.
Maedler et al., "Distinct Effects on Saturated and Monounsaturated Fatty Acids on β-Cell Turnover and Function," Diabetes, vol. 50, Jan. 2001, pp. 69-76.
Maguire et al., "Fatty Acid Profile, Tocopherol, Squalene and Phytosterol Content of Walnuts, Almonds, Peanuts, Hazelnuts and the Macadamia Nut," Int. J. Food Sci. Nutr., May 2004, 55, 3, pp. 171-178, Abstract only, 1 page, retrieved from http://www.ncbi.nlm.nih.gov/pubmed/15223592 on Aug. 23 2012.
Mata et al., "Biodiesel Production from Corn Oil via Enzymatic Catalysis with Ethanol," Energy & Fuels, 2012, 8 pages.
Medina et al., Concentration and Purification of Stearidonic, eicosapentaenoic, and docosahexaenoic Acids from Cod Liver Oil and the Marine Microalgalsochrysis galbana, Journal of the American Oil Chemists' Society, May 1995, vol. 72, Issue No. 5, pp. 575-583.
Mercer et al., "Developments in Oil Extraction from Microalgae," Eur. J. Lipid Sci. Technol., 2011, 9 pages.
Modi et al., "Lipase-mediated Conversion of Vegetable Oils into Biodiesel Using Ethyl Acetate as Acyl Acceptor," Bioresource Technology, 98, 2007, pp. 1260-1264.
Mozzaffarian et al., "Trans-Palmitoleic Acid, Metabolic Risk Factors, and New-Onset Diabetes in U.S. Adults," Ann. of Internal Med., Dec. 2010, vol. 153, No. 12, 11 pgs.
Nestel et al., "Effects of Increasing Dietary Palmitoleic Acid Compared with Palmitic and Oleic Acids on Plasma Lipids of Hypercholesterolemic Men," Journal of Lipid Research, vol. 35, 1994, pp. 656-662, downloaded from www.jlr on May 2, 2012.
Oncel et al., "Comparison of Different Cultivation Modes and Light Intensities Using Mono-cultures and Co-cultures of Haemotococcus pluvialis and Chlorella zofingiensis," Chemical Technology and Biotechnology, Nov. 2010, vol. 86, Issue 3, pp. 414-420, Abstract Only, 3 pages.
Privett, et al., "Solubilities of Fatty Acids and Derivatives in Acetone," Journal of the American Oil Chemists Society, 35, 1958, pp. 4 pages.
Proctor, "According to Drs. Oz & Roizen, Purified Omega 7 Palmitoleic Acid 7 is the "new" good fat!," Jul. 2012, retrieved from www.cardia7.com, 4 pgs.
Rossi et al., "Optimization of Molecular Distillation to Concentrate Ethyl Esters of Eicosapentaenoic (20:5 ω-3) and docosahexaenoic Acids (22:6 ω-3) Using Simplified Phenomenological Modeling," J. Sci. Food Agric., 2011, 91 pp. 1452-1458.
Rubio-Rodriguez et al., "Production of Omega-3 Polyunsaturated Fatty Acid Concentrates: A Review," Innovative Food Science and Emerging Technologies, 11, 2010, 12 pages.
Rusch et al., "A Palmitoleic Acid Ester Concentrate from Seabuckthorn Pomace," Eur. J. Lipid Sci. Technol., 106, 2004, pp. 412-416.
Ruxton et al., "The Impact of Long-chain n-3 Polyunsaturated Fatty Acids on Human Health," Nutrition Research Reviews, 2005, 18, pp. 113-129.
Schlenk et al., "The Urea Complexes of Unsaturated Fatty Acids," Science, New Series, vol. 112, No. 2897, Jul. 1950, pp. 19-20, 3 pages.
Sengör et al., "Fatty Acid Compositions of Flathead Grey Mullet (Mugil cephalus L., 1758) Fillet, Raw and Beeswaxed Caviar Oils," Turkish Journal of Fisheries and Aquatic Sciences, 3, 2003, pp. 93-96.
Simopoulos, "Evolutionary Aspects of Diet, the Omega-6/omega-3 Ratio and Genetic Variation: Nutritional Implications for Chronic Diseases," Biomedicine & Pharmacotherapy, 60, 2006, pp. 502-507.
Simopoulos, "Dossier: Polyunsaturated Fatty Acids in Biology and Diseases. The Importance of the Ratio of Omega-6/omega-3 Essential Fatty Acids," Biomed Pharmacother, 56, 2002, pp. 365-379.
Shahidi et al., "Omega-3 Fatty Acid Concentrates: Nutritional Aspects and Production Technologies," Trends in Food Science & Technology, 9, 1998, pp. 230-240.
Temple, "Dietary Fats and Coronary Heart Disease," Biomed & Pharmacother, 1996, 50, pp. 261-268.
Wanasundara et al., "Concentration of Omega 3-polyunsaturated Fatty Acids of Seal Blubber Oil by Urea Complexation: Optimization of Reaction Conditions," Food Chemistry, 65, 1999, pp. 41-49.
Wijendran et al., "Dietary n-6 and n-3 Fatty Acid Balance and Cardiovascular Health," Annual Review of Nutrition, 2004, 24, pp. 597-615, 21 pages.
Wille et al., "Palmitoleic Acid Isomer (C16:1delta6) in Human Skin Sebum Is Effective Against Gram-positive Bacteria," Skin Pharmacol. Appl. Skin Physiol., May-Jun. 2003, 3, pp. 176-187, Abstract, 2 pages, retrieved from http://www.ncbi.nlm.nih.gov/pubmed/12677098, on Aug. 23, 2012.
Yang et al., "Fatty Acid Composition of Lipids in Sea Buckthorn (Hippophaë rhamnoides L.) Berries of Different Origins," J. Agric. Food Chem., 2001, 49, pp. 1939-1947.
Yang et al., "Chronic Administration of Palmitoleic Acid Reduces Insulin Resistance and Hepatic Lipid Accumulation in KK-A$^y$ Mice with Genetic Type 2 Diabetes," Lipids in Health and Disease, 2011, 10, 120, 8 pages.
Yoon et al., "Effect of Palmitoleic Acid on Melanogenic Protein Expression in Murine B16 Melanoma," Journal of Oleo Science, 59, 6, 2010, pp. 315-319.
Zabeti et al., "Activity of Solid Catalysts for Biodiesel Production: A Review," Fuel Processing Technology, 90, 2009, pp. 770-777.
Zeb, "Chemical and Nutritional Constituents of Sea Buckthorn Juice," Pakistan Journal of Nutrition, 2004, vol. 3, Issue No. 2, pp. 99-106, Abstract Only, 2 pages, retrieved from http://www.scialert.net/abstract/?doi=pjn.2004.99.106 on Aug. 23, 2012
Zhekisheva et al., "Accumulation of Oleic Acid in Haematococcus pluvialis (Chlorophyceae) under Nitrogen Starvation or High Light is Correlated with that of Astaxanthin Esters[1]," J. Phycol., 38, 2002, pp. 325-331.
Sarada et al., 'Phycocyanin from Spirulina sp: Influence of Processing of Biomass on Phycocyanin Yield, Analysis of Efficacy of Extraction Methods and Stability Studies on Phycocyanin,' Process Biochemistry, 34, 1999, pp. 795-801.

(56) References Cited

OTHER PUBLICATIONS

Bermejo Roman, et al., "Recovery of Pure B-phycoerythrin from the microalga Porphyridium Cruentum," Journal of Biotechnology, 93, 2002, pp. 73-85.
"Algae Oil Extraction," Diversified Technologies, Inc., Bioscience Technology, Jan. 3, 2011, New Source Web Content—US, document also available from: www.ea.qov.au/atmosphere/transport/biodiesel/index.html, 1 page.
Agboola, S. et al., "Characterisation and Functional Properties of Australian Rice Protein Isolates," Journal of Cereal Science 41, 2005, pp. 283-290.
Al-Fadhli, et al., "Glycolipids From the Red Alga Chondria Armata (Kutz.) Okamura," Glycobiology, vol. 16, No. 10, 2006, pp. 902-915.
Amin, S., "Review on Biofuel Oil and Gas Production Processes from Microalgae,"Energy Conversion and Management, 50, 2009, pp. 1834-1840.
Author Unknown, "Renewable Biological Systems for Alternative Sustainable Energy Production," Chapter 5—Hydrogen Production, Agriculture and Consumer Protection, Food and Agriculture Organization of the United Nations (FAO), Copyright 1997, ISBN 92-5-104059-1, retrieved from http://www.fao.org/docrep/w7241e/w7241e0g.htm, Accessed May 23, 2012, 9 pages.
Author Unknown, "Seaweed Classification," Cornish Seaweed Resources, Seaweeds, Greens, Browns & Reds, 2011, 3 pages, retrieved from: http://www.cornishseaweedresources.org/redgreenbrown.htm, author unknown.
Barbarino et al., "An Evaluation of Methods for Extraction and Quantification of Protein from Marine Macro- and Microalgae," Journal of Applied Phycology, 2005, 17, pp. 447-460.
Belitz, et al., "Food Chemistry," 1 Amino Acids, Peptides, Proteins, 4th Revised and Extended Edition, Springer-Verlag, Feb. 2009, pp. 8-34, 29 pages.
Berberoglu, H. et al., "Radiation Characteristics of Chlamydomonas Reinhardtii CC125 and its Truncated Chlorophyll Antenna Transformants tla1, tlaX and tla1-CW+" International Journal of Hydrogen Energy 33, 2008, pp. 6467-6483.
Bligh, E.G. et al., "A Rapid Method of Total Lipid Extraction and Purification," Canadian Journal of Biochemistry and Physiology, vol. 37, No. 8, Jul. 1959, pp. 911-917, 8 pages.
Borowitzka, M.A. "Commercial Production of Microalgae: Ponds, Tanks, Tubes and Ferments," Journal of Biotechnology 70 (1999), pp. 313-321, 10 pages.
Brennan et al., "Biofuels from Microalgae—A Review of Technologies for Production, Processing, and Extractions of Biofuels and Co-products," Renewable and Sustainable Energy Reviews, 14, 2010, pp. 557-577.
Castriotta et al., "Protein Classification and Nitrogen Extractability of Grape Seed Meal," J. Agric. Food Chem., 1978, vol. 26, No. 3, pp. 763-765.
Catchpole, et al., "The Extraction and Fractionation of Specialty Lipids Using Near Critical Fluids," J. of Supercritical Fluids 47, 2009, pp. 591-597.
Chisti, Y. "Biodiesel from Microalgae," Biotechnology Advances 25, 2007, pp. 294-306.
Christie, W.W., "Lipid Analysis", Third Edition, Oily Press, Bridgewater, UK, 2003, pp. 97-102, 7 pages.
Communication Relating to the Results of the Partial International Search for corresponding International Patent Application No. PCT/US2011/031412 mailed Aug. 9, 2011, 4 pages.
Communication Relating to the Results of the Partial International Search performed by International Searching Authority, the European Patent Office, for International Application No. PCT/US2012/065889, mailing date May 27, 2013, 4 pages.
Cooney, et al., "Extraction of Bio-Oils from Microalgae," Separation and Purification Reviews, vol. 38(4), Oct. 2009, pp. 291-325, 37 pages.
Daigger, G.T. et al., "Are Membrane Bioreactors Ready for Widespread Application?" Environmental Science & Technology, Oct. 1, 2005, pp. 399A-406A, 9 pages.

Database WPI, Week 199421, Thomson Scientific, London, GB; AN 1994-172764, XP002677124, & JP 6113872A (Towa Kasei Kogyo KK), Apr. 1994, Abstract, 2 pages.
Database WPI, Week 200326, Thomson Scientific, London, GB; AN 2003-259841 & JP 2002 220402 A (Oriental Bio KK) Aug. 9, 2002, abstract, 2 pages.
Database WPI, Week 200966, Thomson Scientific, London, GB; AN 2009-J23632, XP002677125, & KR 100896327B1 (Diatech Koera Co. Ltd.), May 2009, Abstract, 2 pages.
Database WPI, Week 201102, Thomson Scientific, London, GB; AN 2010-N15002, XP002677126, & KR 100950441B1 (Accutech Co. Ltd.), Apr. 2010, Abstract, 2 pages.
de Morais Coutinho et al., "State of Art of the Application of Membrane Technology to Vegetable Oils: A Review," Food Research International, 42, 2009, pp. 536-550.
Environment Australia, "Setting National Fuel Quality Standards," Paper 6, National Standard for Biodiesel—Discussion Paper, Mar. 2003, downloaded from U.S. Appl. No. 11/979,699, No Author, pp. 1-103, 119 pages.
Fajardo et al, "Lipid Extraction From the Microalga Phaeodactylum Tricornutum," European Journal of Lipid Science and Technology, 2007, vol. 109, No. 2, pp. 120-126.
Gibbs, et al., "Natural Protoplast Dunaliella as a Source of Protein," Appl. Environ Microbiol., Apr. 1976, Abstract Only, 1 page.
Grima et al., "Recovery of Microalgal Biomass and Metabolites: Process Options and Economics," Biotechnology Advances 20, 2003, pp. 491-515.
Gross et al., "The Nutritional Quality of Scenedesmus Acutus in a Semi-Industrial Plant in Peru," J. Environ. Pathol. Toxicol. Oncol., May-Aug. 1986, Abstract Only, 1 page.
Guckert, et al., "Lipid Solvent Systems are Not Equivalent for Analysis of Lipid Classes in the Microeukaryotic Green Alga, Chlorella," Journal of Microbiological Methods, 8, 1988, pp. 139-149.
Halim, et al., "Oil Extraction from Microalgae for Biodiesel Production," Bioresource Technology, 102, 2011, pp. 178-185.
Harun, R. et al., "Bioprocess Engineering of Microlagae to Produce a Variety of Consumer Products," Renewable and Sustainable Energy Reviews, 14, 2010, pp. 1037-1047.
Hejazi, M.A. et al., "Milking of Microalgae," Trends in Biotechnology vol. 22, No. 4, Apr. 2004, pp. 189-194.
Herfindal, L. et al., "A High Proportion of Baltic Sea Benthic Cynaobacterial Isolates Contain Apoptogens Able to Induce Rapid Death of Isolated Rat Hepatocytes," Toxicon 46, 2005, pp. 252-260.
Herrero, M. et al., "Sub- and Supercritical Fluid Extraction of Functional Ingredients From Different Natural Sources: Plants, Food-by-products, Algae and Microalgae—A Review," Food Chemistry, 98, 2006, pp. 136-148.
Huang, G. et al., "Biodiesel Production by Microalgal Biotechnology," Applied Energy 87, 2010, pp. 38-46.
Huang, G. et al., "Rapid Screening Method for Lipid Production in Alga Based on Nile Red Fluorescence," Biomass and Bioenergy, 33, 2009, pp. 1386-1392.
International Search Report and Written Opinion for International Patent Application No. PCT/US2011/031404 mailed Aug. 3, 2011, 12 pages.
International Search Report and Written Opinion for International Patent Application No. PCT/US2011/031407 mailed Aug. 9, 2011, 10 pages.
International Search Report and Written Opinion for International Patent Application No. PCT/US2011/031408 mailed Aug. 9, 2011, 10 pages.
International Search Report and Written Opinion for International Patent Application No. PCT/US2011/031414 mailed Aug. 5, 2011, 11 pages.
International Search Report and Written Opinion for International Patent Application No. PCT/US2011/031417 mailed Aug. 3, 2011, 11 pages.
International Search Report and Written Opinion for International Patent Application No. PCT/US2011/031419 mailed Sep. 5, 2011, 13 pages.
International Search Report and Written Opinion for International Patent Application No. PCT/US2011/031421 mailed Aug. 3, 2011, 11 pages.

(56) References Cited

OTHER PUBLICATIONS

International Search Report and Written Opinion of the International Searching Authority, the European Patent Office, for International Application No. PCT/US2011/059144, mailing date Feb. 15, 2012, 14 pages.
International Search Report and Written Opinion of the International Searching Authority, the European Patent Office, for International Application No. PCT/US2011/059148, mailing date Jun. 25, 2012, 13 pages.
International Search Report and Written Opinion of the International Searching Authority, the European Patent Office, for International Application No. PCT/US2011/059152, mailing date May 22, 2012, 17 pages.
International Search Report and Written Opinion of the International Searching Authority, the European Patent Office, for International Application No. PCT/US2012/027537, mailing date Jun. 14, 2012, 13 pages.
International Search Report and Written Opinion of the International Searching Authority, the European Patent Office, for International Application No. PCT/US2012/058644, dated Jan. 23, 2013, 12 pages.
International Search Report and Written Opinion of the International Searching Authority, the European Patent Office, for International Application No. PCT/US2013/033301, dated Aug. 1, 2013, 14 pages.
International Search Report and Written Opinion of the International Searching Authority, the European Patent Office, for International Application No. PCT/US2013/033311, dated Jul. 31, 2013, 13 pages.
Jimenez, et al., "Different Ways to Die: Cell Death Modes of the Unicellular Chlorophyte Dunaliella Viridis Exposed to Various Environmental Stresses are Mediated by the Caspase-like Activity DEVDase," Journal of Experimental Botany, vol. 60, No. 3, 2009, pp. 815-828.
Ju et al., "Extraction, Denaturation and Hydrophobic Properties of Rice Flour Proteins," Journal of Food Science, vol. 66, No. 2, 2001, pp. 229-232.
Kanda et al., "Simple Extraction Method of Green Crude from Natural Blue-Green Microalgae by Dimethyl Ether," Fuel, 90, 2011, pp. 1264-1266.
Kanda et al., "Lipids Extracted from Several Species of Natural Blue-Green Microalgae by Dimethyl Ether: Extraction Yield and Properties," Fuel, 95, 2012, pp. 88-92.
Knuckey et al., "Production of Microalgal Concentrates by Flocculatian and Their Assessment as Aquaculture Feeds," Aquacultural Engineering, vol. 35, Issue 3, Oct. 2006, pp. 300-313.
Koris, et al., Dry Degumming of Vegetable Oils by Membrane Filtration, Desalination 148, 2002, pp. 149-153.
Kumari et al., "Tropical Marine Macroalgae as Potential Sources of Nutritionally Important PUFAs," Food Chemistry, 120, 2010, pp. 749-757.
Lee, et al., "Comparison of Several Methods for Effective Lipid Extraction from Microalgae," Bioresource Technology, 101, 2010, pp. S75-S77.
Lee et al., "Isolation and Characterization of a Xanthophyll Aberrant Mutant of the Green Alga Nannochloropsis oculata," Marine Biotechnology, 2006, pp. 238-245.
Lorenz, "A Technical Review of Haematococcus Algae," NatuRoseTM Technical Bulletin #060, Revision Date: Mar. 30, 1999, retrieved from the Internet: &Ithttp://www.cyanotech.com/pdfs/bioastin/axbul60.pdf>, retrieved on Dec. 14, 2011, 12 pages.
Mata et al., "Microalgae for Biodiesel Production and Other Applications: A Review" Renewable and Sustainable Energy Reviews, 2009, 16 pages.
Mattos et al., "Glycolipids From Macroalgae: Potential Biomolecules for Marine Biotechnology?," Rev. Bras. Farmacogn. Braz. J. Pharmacogn., 21(2), Mar./Apr. 2011, pp. 244-247.
Meneses et al., "Algal Phospholipids by 31P NMR: Comparing Isopropanol Pretreatment with Simple Chloroform/Methanol Extraction," Int. J. Biochem., vol. 25, No. 6, pp. 903-910, 1993.
Mercer et al., "Developments in Oil Extraction from Microalgae," Eur. J. Lipid Sci. Technol. 2011, 113, 539-547.
Nakhost et al., "Non-Conventional Approaches to Food Processing in Cells. I-Algal Proteins; Characterization and Process Optimization," Advances in Space Research, 1987, vol. 7, pp. 27-36.
Plaza et al., "Screening for Bioactive Compounds from Algae," Journal of Pharmaceuticals and Biomedical Analysis, 51, 2010, pp. 450-455.
Porra, "A Simple Method for Extracting Chlorophylls from the Recalcitrant Alga, Nannochloris atomus, without Formation of Spectroscopically-Different Magnesium-Rhodochlorin Derivatives," Biochemica et Biophysica Acta, 1019, 1990, pp. 137-141.
Raynie, "Modern Extraction Techniques," Anal. Chem., Jun. 2006, vol. 78, No. 12, pp. 3997-4003.
Rebolloso-Fuentes et al., "Biomass Nutrient Profiles of the Microalga Nannochloropsis," J. Agric. Food Chem., 2001, vol. 49, No. 6, pp. 2966-2972.
Rhodes, "Oil from Algae; Salvation from Peak Oil?" Science Progress, 2009, 92 (1), pp. 39-90.
Rittmann, "Opportunities for Renewable Bioenergy Using Microorganisms," Biotechnology and Bioengineering, vol. 100, No. 2, Jun. 2008, pp. 203-212.
Rittmann et al., "Environmental Biotechnology: Principles and Applications," McGraw-Hill Book Co., New York, 2001, 39 pages.
Rossignol et al., "Membrane Technology for the Continuous Separation Microalgae/culture Medium: Compared Performances of Cross-flow Microfiltration and Ultrafiltration," Aquacultutal Engineering, vol. 20, No. 3, 1999, pp. 191-208, 19 pages.
Ryckebosch et al., "Optimization of an Analytical Procedure for Extraction of Lipids from Microalgae," J. Am. Oil Chem. Soc., 2012, 89, pp. 189-198.
Shewry et al., "The Prolamin Storage Proteins of Cereal Seeds: Structure and Evolution," Biochem. J., 1990, vol. 267, 12 pages.
Shyur et al., "Rice Prolamins: Heterogeneity of cDNAs and Synthesis of Precursors," Bot. Bull. Acad. Sin., 1993, 34, pp. 143-153.
Sostaric et al., Growth, Lipid Extraction and Thermal Degradation of the Microalga Chlorella vulgaris, New Biotechnology, vol. 29, No. 3, Feb. 2012, pp. 325-331.
Spolaore et al., Commercial Applications of Microalgae, Journal of Bioscience and Bioengineering, vol. 101, No. 2, 2006, pp. 87-96.
Steinitz et al., "A Mutant of the Cyanobacterium Plectonema Boryanum Resistant to Photooxidation," Plant Science Letters, vol. 16, Issues 2-3, Oct. 1979, pp. 327-335, 11 pages.
Supplementary International Search Report of the Supplemental International Searching Authority, the National Board of Patents and Registration of Finland, for International Application No. PCT/US2011/059152, dated Jul. 5, 2012, 4 pages.
Supplementary International Search Report of the Supplementary International Searching Authority, the Austrian Patent Office, for International Application No. PCT/US2011/059144, dated Nov. 8, 2012, 4 pages.
Tchorbanov et al., "Enzymatic Hydrolysis of Cell Proteins in Green Algae Chlorella and Scenedesmus After Extraction with Organic Solvents," Enzyme Microb. Technol., Apr. 1988, vol. 10, pp. 233-238.
Uduman et al. "Dewatering of Microalgal Cultures: A Major Bottleneck to Algae-based Fuels," Journal of Renewable and Sustainable Energy, 2, 2010, pp. 012701-1-012701-15.
Voorhees et al., "Analysis of Insoluble Carbonaceous Materials from Airborne Particles Collected in Pristine Region of Colorado," Journal of Analytical and Applied Pyrolysis, 18, 1991, pp. 189-205.
Wachowicz et al. "The Protein of the Alga Spirulina Platensis," Database FSTA [Online] International Food Information Service (IFIS), Frankfurt-Main, DE; 1974, Abstract Only, 1 page.
Wang et al., "Lipid and Biomass Distribution and Recovery from Two Microalgae by Aqueous and Alcohol Processing," J. Am. Oil Chem. Soc., 2012, 89, pp. 335-345.
Wang et al., "Technologies for Extracting Lipids from Oleaginous Microorganisms for Biodiesel Production," Front. Energy, 2012, 6(3), pp. 266-274.
Webvitamins (2011, updated) "Globulin Protein Concentrate," www.webvitamins.com/Nutrient.aspx?id=2007, 1 page, Author Unknown.
Wegmann et al., "Short Communication: Effect of Temperature on Glycerol Retention in the Halotolerant Algae Dunaliella and Asteromonas," Plant Physiol., 1980, vol. 66, pp. 1196-1197.
Yang et al., "Chronic Administration of Palmitoleic Acid Reduces Insulin Resistance and Hepatic Lipid Accumulation in KK-Ay Mice with Genetic Type 2 Diabetes," Lipids in Health and Disease, 2011,10:120, 8 pages.
Young et al., "Lipid Extraction from Biomass Using Co-Solvent Mixtures of Ionic Lipids and Polar Covalent Molecules," Separation and Purification Technology, 72, 2010, pp. 118-121.

OMEGA 7 RICH COMPOSITIONS AND METHODS OF ISOLATING OMEGA 7 FATTY ACIDS

CROSS-REFERENCE TO RELATED APPLICATIONS

This application claims priority to U.S. Patent Application No. 61/561,145 filed Nov. 17, 2011 and U.S. Patent Application No. 61/610,160 filed Mar. 13, 2012. This application is related to U.S. patent application Ser. No. 13/194,691, filed Oct. 14, 2011, entitled Methods of Using *Nannochloropsis* Algal Strains to Produce Hydrocarbons and Fatty acids, which claims the benefit of U.S. Provisional Application No. 61/369,533, filed Jul. 30, 2010, and is also related to U.S. patent application Ser. No. 13/081,197, filed Nov. 1, 2011, entitled extraction of Neutral Lipids by a Two Solvent Method, which is a continuation-in-part of U.S. patent application Ser. No. 13/081,197, filed Apr. 6, 2011, entitled Extraction with Fractionation of Oil and Proteinaceous material from Oleaginous Material, which claims the benefit of U.S. Provisional Application No. 61/321,290, filed Apr. 6, 2010, entitled Extraction with Fractionation of Oil and Proteinaceous material from Oleaginous Material, and U.S. Provisional Application No. 61/321,286, filed Apr. 6, 2010, entitled Extraction With Fractionation of Oil and Co-Products from Oleaginous Material, the entire contents of which are hereby incorporated by reference herein.

FIELD OF INVENTION

Compositions rich in palmitoleic acid (an omega-7 monosaturated fatty acid), and methods and systems for isolation of palmitoleic acid from algal sources are disclosed. Embodiments of the invention include techniques for isolation of palmitoleic acid from algal sources. One implementation includes transesterification of an algal lipid extract and distillation of the esterification product. The omega-7 ester rich fraction is then processed in a crystallization step to isolate at least one omega-7 product.

BACKGROUND

Palmitoleic acid (also known as (Z)-9-hexadecanoic acid, cis-palmitoleic acid, 9-cis-palmitoleic acid, hexadec-9-enoic acid and C16:1) is an omega-7 monosaturated fatty acid with the chemical formula $CH_3(CH_2)_5CH=CH(CH_2)_7COOH$. Palmitoleic acid also exists in a trans form (known as trans-palmitoleic acid, 9-trans-palmitoleic acid or (E)-9-hexadecanoic acid, which demonstrates improved thermodynamic stability over the cis isomer. Trans-palmitoleic acid is found in certain dairy products. The conversion from cis- to trans-palmitoleic acid can be achieved thermally, chemically or enzymatically. Palmitoleic acid is present in variety of vegetable oils, animal fats and marine oils in small quantities. Two plant sources having high concentrations of palmitoleic acid are sea buckthorn (*Hippophae rhamnoids*), which belongs to the Elaeagnacae family and Rosales order (a taxonomic order which includes strawberries, blackberries, apples, pears, peaches, apricots, and almonds) and macadamia nut oil (*Macadamia integrifolia*), which is native to Australia. Palmitoleic acid concentration of sea buckthorn is about 40% and macadamia oil contains about 20%. Another source of palmitoleic acid is mink oil, which contains about 15% palmitoleic acid. All these sources have limited availability and are premium sources. The plant sources are being used as food supplements (sea buckthorn fruit is used as "superfood") or premium food ingredient (macadamia nuts are used in chocolate and other high value foods) or in cosmetics (mink oil). Palmitoleic acid is biosynthesized from palmitic acid by the action of the enzyme delta-9 desaturase.

Palmitoleic acid has shown utility in medical applications. For example, palmitoleic acid has been shown to improve hyperglycemia (high glucose concentration in blood) and hypertriglyceridemia and increase sensitivity, by suppressing proinflammatory gene expressions and improving hepatic lipid metabolism in diabetic mice. Yang, Z-H. et al. "Chronic administration of palmitoleic acid reduces insulin resistance and hepatic lipid accumulation in KK-Ay Mice with genetic type 2 diabetes" *Lipid Health Disease* 2011, 10, 120.

Palmitoleic acid has also been shown to prevent beta-cell apoptosis induced by glucose or saturated fatty acids (beta-cells or pancreas secrete insulin and their programmed death or apoptosis leads to type-2 diabetes). Morgan, N. G.; Dhayal, S. "Unsaturated fatty acids as cytoprotective agents in the pancreatic β-cell" *Prostaglandins Leukot. Essent. Fatty Acids* 2010, 82, 231-236; Morgan, N. G. et al. "The cytoprotective actions of long-chain mono-unsaturated fatty acids in pancreatic β-cells" *Biochem. Soc. Trans.* 2008, 36, 905-908.

Palmitoleic acid-rich diets have also been reported to improve circulating lipid profile, resulting in reduced total and LDL cholesterol. Matthan, N. R. et al. "Effects of dietary palmitoleic acid on plasma lipoprotein profile and aortic cholesterol accumulation are similar to those of other unsaturated fatty acids in the F1B Golden Syrian Hamster" *J. Nutr.* 2009, 139 (2), 215-221; Griel, A. E. et al. "A macadamia nut-rich diet reduces total and LDL-cholesterol in mildly hypercholesterolemic men and women" *J. Nutr.* 2008, 138 (4), 761-767; Garg, M. L. et al. "Macadamia nut consumption lowers plasma total and LDL cholesterol levels in hypercholesterolemic men" *J. Nutr.* 2003, 133 (4), 1060-1063.

Trans-palmitoleic acid concentration in blood levels have been independently associated with higher HDL-cholesterol levels, lower triglyceride levels, and a lower total-cholesterol/HDL-cholesterol ratio. In addition, trans-palmitoleic acid has also been associated with less insulin resistance and a lower risk of new-onset diabetes mellitus. Mozaffarian, D. et al. "Trans-palmitoleic acid, metabolic risk factors, and new-onset diabetes in U.S. adults: a cohort study: *Ann. Intern. Med.* 2010, 153 (12), 790-799.

In addition, palmitoleic acid has been shown to be useful in skin care and cosmetic applications as a highly effective antioxidant. Research has suggested that palmitoleic acid may be involved in the cell rejuvenation and healing process, particularly in dry and/or mature skin. Palmitoleic acid supports cell regeneration and can help heal burns and wounds, and reduces dermatitis and eczema. It also offers some protection form the harmful effects of the sun. When applied directly to the skin, palmitoleic acid can increase triglyceride concentration in the lipid barrier of the skin, one of the naturally occurring stratum corneum lipid components, consequently enhancing the protective nature of the stratum corneum.

As more beneficial applications for palmitoleic acid are discovered, the demand for palmitoleic acid may increase beyond the limited supply readily available from sea buckthorn, macadamia nut oil, and mink oil. Alternative sources for palmitoleic acid in which a high concentration of palmitoleic acid may be readily obtained year round at lower costs could provide a new supply source. With the recognized benefits of palmitoleic acid, there is a need in the art for compositions with a concentration high in omega-7 fatty acids and an efficient method of obtaining the omega-7 fatty acids from a readily available source.

BRIEF SUMMARY

Disclosed here are compositions rich in omega-7 fatty acids, including palmitoleic acid, and products rich in omega-7 fatty acids derived from algal biomass. In some embodiments, the total fatty acid profile of the composition includes a fraction comprising at least about 60% fatty acids of the types C16:0 and C16:1. In some embodiments, the total fatty acid profile of the composition includes a fraction comprising at least about 80% fatty acids of the types C16:0, C16:1, C18:0, and C18:1. In some embodiments, the composition comprises algal oil of: at least about 30% C16:0; at least about 25% C16:1; at least about 1% C18:0; and at least about 15% C18:1. In some embodiments, the total fatty acid profile of the composition includes a fraction comprising at least about 43% fatty acids of the types C16:1 and C18:1.

The algae and/or compositions rich in omega-7 fatty acids may be used in products or as ingredients of products. The products may comprise cosmetic, medicinal, pharmaceutical, nutritional, food, feed and beverage products. Methods and systems for increasing the production or concentration of omega-7 fatty acids, and isolating omega-7 fatty acids from algal biomass are also disclosed herein.

DETAILED DESCRIPTION

Overview

Algae have been found to produce a variety of fatty acids, including C16:1 fatty acids. The composition of fatty acids varies among different strains of algae, with some strains producing higher concentrations of palmitoleic acid. Due to the composition of their fatty acid profile, algae such as *Nannochloropsis* provide an attractive source of omega-7 fatty acids due to algae's ability to grow quickly and year round. Therefore, algae can provide a more cost effective and more readily available source of omega-7 fatty acids than sea buckthorn oil, macadamia nut oil, and mink oil.

Through experimentation it has been determined that algae may be cultivated to produce a desirable fatty acid profile comprising individual fatty acids or groups of fatty acids which may be isolated through various extraction processes. The isolated fatty acids may comprise a composition rich in omega-7 fatty acids. The cultivated algae and/or isolated composition may be used individually as products or as an ingredient in a variety of products.

Methods of Increasing Concentration/Production of Omega-7 Fatty Acids in Algae

The average microalgae produce between 1% and 70% lipids relative to the dry cell weight. To affect algae's fatty acid profile and production, multiple approaches may be taken. One approach is to alter the algae itself. Algae strains may be genetically modified to alter characteristics, such as fatty acid profile, in order to attain a composition with a desired fatty acid profile.

Another approach is to alter the algae's environment. Some species of microalgae, when exposed to certain conditions, can produce up to 90% of their dry weight as lipids. In one example, cultures of *Nannochloropsis limnetica* with varied levels of $K_2HPO_4$ have shown that the total content of fatty acids and relative percent of C16:1 increased as the concentration of $K_2HPO_4$ increased. *Nannochloropsis limnetica* have also been shown to produce a fatty acid profile of approximately 25% C16:1 fatty acid with CO2 enrichment through aeration in exponential phase and a lower percent (approximately 20%) of C16:1 fatty acid without CO2 enrichment through aeration in stationary phase. *Nannochloropsis* also showed a higher level of neutral lipid concentration in cultures with a lower initial concentration of nitrogen. Therefore, by adjusting the culture conditions such as, but not limited to: type of light, duration of light, intensity of light, medium composition, mixing regime, chemical concentrations, gas concentrations, aeration, methods of administering gas, methods of administering nutrients, type of nutrients, and concentration of nutrients provided to a culture of algae with a favorable fatty acid disposition; a fatty acid profile of a desirable composition may be attained.

Compositions/Products Enriched with Omega-7 Fatty Acids

Figure 4:
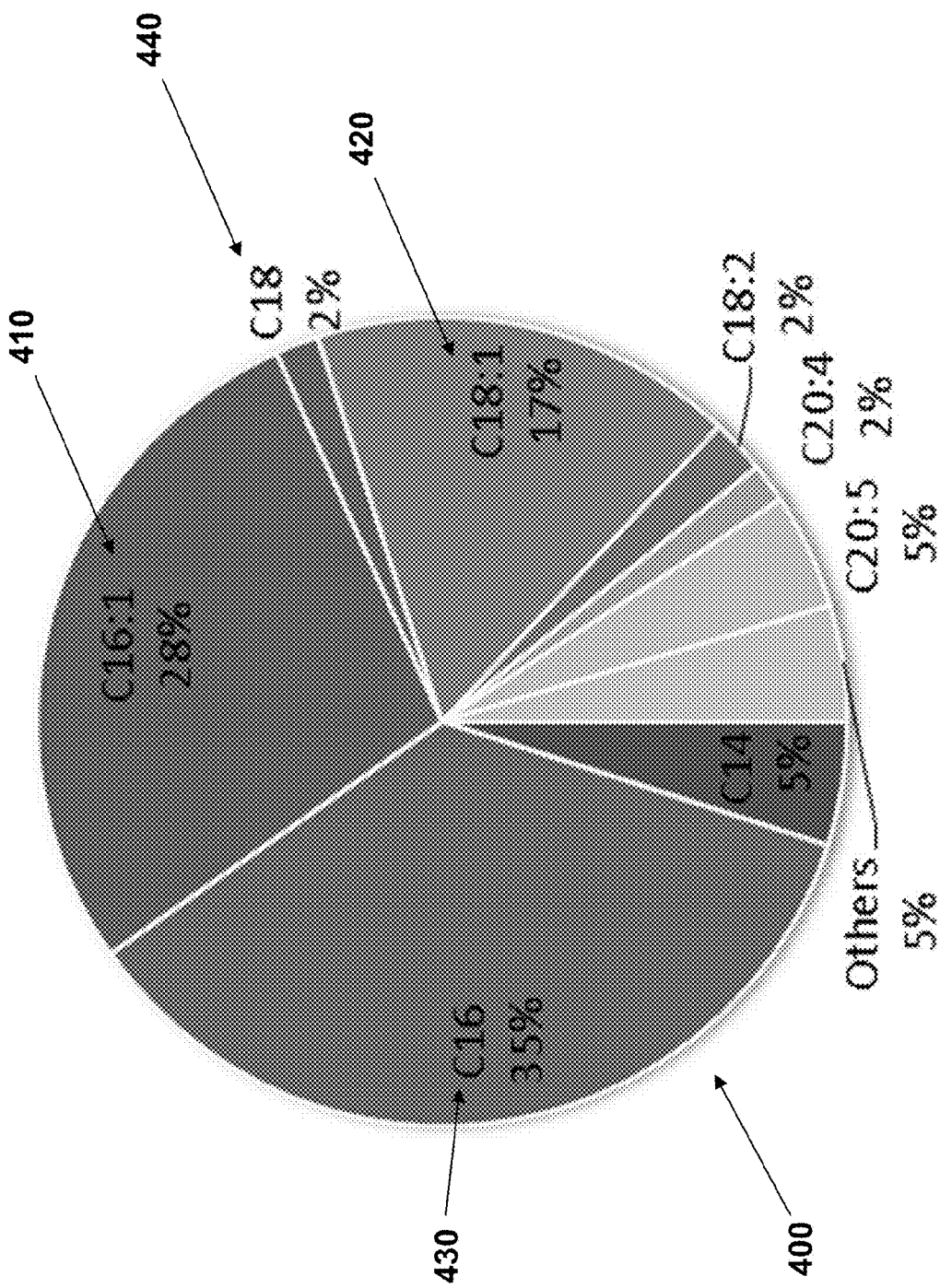
FIG. 4 is a pie chart of the relative amounts of acids present in an exemplary mixture of algae oils generated from *Nannochloropsis*.

*Nannochloropsis* was cultivated in a culture under conditions suitable to promote production of fatty acids and harvested to allow algal oil to be extracted for analysis. Referring next to FIG. 4, this pie chart 400 demonstrates the percentage of various oils present in an exemplary mixture of algae oils generated from *Nannochloropsis*. Slice 430 shows the percentage of C16:0 acids (such as palmitic acid) present in the mixture as about 35%. Slice 410 shows the percentage of C16:1 acids (such as palmitoleic acid) present in the mixture as about 28%. Slice 440 shows the percentage of C18:0 acids (such as stearic acid) present in the mixture as about 2%. Slice 420 shows the percentage of C18:1 acids (such as oleic acid) present in the mixture as about 17%.

In some embodiments, the percentage of C16:0 acids present in the algae oil mixture comprises at least about 30%. In some embodiments, the percentage of C16:1 acids present in the algae oil mixture comprises at least about 25%. In some embodiments, the percentage of C18:0 acids present in the algae oil mixture comprises at least about 1%. In some embodiments, the percentage of C18:1 acids present in the algae oil mixture comprises at least about 15%.

In other embodiments, the percentage of C16:0 acids present in the algae oil mixture comprises about 10% to about 50%. In other embodiments, the percentage of C16:1 acids present in the algae oil mixture comprises about 10% to about 50%. In other embodiments, the percentage of C18:0 acids present in the algae oil mixture comprises about 0% to about 15%. In other embodiments, the percentage of C18:1 acids present in the algae oil mixture comprises about 0% to about 20%.

In some embodiments, the total fatty acid composition of the algae oil comprises at least about 50% fatty acids of the types C16:0 and C16:1. In some embodiments, the total fatty acid composition of the algae oil comprises at least about 60% fatty acids of the types C16:0 and C16:1. In some embodiments, the total fatty acid composition of the algae oil comprises at least about 70% fatty acids of the types C16:0 and C16:1. In some embodiments, the total fatty acid composition of the algae oil comprises at least about 80% fatty acids of the types C16:0 and C16:1. In some embodiments, the total fatty acid composition of the algae oil comprises at least about 90% fatty acids of the types C16:0 and C16:1.

In further embodiments, the fraction comprising C16:0 and C16:1 fatty acids comprises at least about 40% C16:1 fatty acids. In further embodiments, the fraction comprising C16:0 and C16:1 fatty acids comprises at least about 50% C16:1 fatty acids. In further embodiments, the fraction comprising C16:0 and C16:1 fatty acids comprises at least about 60% C16:1 fatty acids. In further embodiments, the fraction comprising C16:0 and C16:1 fatty acids comprises at least about 70% C16:1 fatty acids. In further embodiments, the fraction comprising C16:0 and C16:1 fatty acids comprises at least about 80% C16:1 fatty acids. In further embodiments, the fraction comprising C16:0 and C16:1 fatty acids comprises at least about 90% C16:1 fatty acids.

In some embodiments, the total fatty acid composition of the algae oil comprises at least about 50% fatty acids of the type C16:0, C16:1, C18:0, and C18:1. In some embodiments, the total fatty acid composition of the algae oil comprises at least about 60% fatty acids of the types C16:0, C16:1, C18:0, and C18:1. In some embodiments, the total fatty acid composition of the algae oil comprises at least about 70% fatty acids of the types C16:0, C16:1, C18:0, and C18:1. In some embodiments, the total fatty acid composition of the algae oil comprises at least about 80% fatty acids of the types C16:0, C16:1, C18:0, and C18:1. In some embodiments, the total fatty acid composition of the algae oil comprises at least about 90% fatty acids of the types C16:0, C16:1, C18:0, and C18:1.

In further embodiments, the fraction comprising C16:0, C16:1, C18:0, and C18:1 fatty acids comprises at least about 30% C16:1 fatty acids. In further embodiments, the fraction comprising C16:0, C16:1, C18:0, and C18:1 fatty acids comprises at least about 40% C16:1 fatty acids. In further embodiments, the fraction comprising C16:0, C16:1, C18:0, and C18:1 fatty acids comprises at least about 50% C16:1 fatty acids. In further embodiments, the fraction comprising C16:0, C16:1, C18:0, and C18:1 fatty acids comprises at least about 60% C16:1 fatty acids. In further embodiments, the fraction comprising C16:0, C16:1, C18:0, and C18:1 fatty acids comprises at least about 70% C16:1 fatty acids. In further embodiments, the fraction comprising C16:0, C16:1, C18:0, and C18:1 fatty acids comprises at least about 80% C16:1 fatty acids. In further embodiments, the fraction comprising C16:0, C16:1, C18:0, and C18:1 fatty acids comprises at least about 90% C16:1 fatty acids.

In some embodiments, the total fatty acid composition of the algae oil comprises at least about 43% fatty acids of the types C16:1 and C18:1. In some embodiments, the total fatty acid composition of the algae oil comprises at least about 45% fatty acids of the types C16:1 and C18:1. In some embodiments, the total fatty acid composition of the algae oil comprises at least about 50% fatty acids of the types C16:1 and C18:1. In some embodiments, the total fatty acid composition of the algae oil comprises at least about 60% fatty acids of the C16:1 and C18:1. In some embodiments, the total fatty acid composition of the algae oil comprises at least about 70% fatty acids of the types C16:1 and C18:1. In some embodiments, the total fatty acid composition of the algae oil comprises at least about 80% fatty acids of the types C16:1 and C18:1. In some embodiments, the total fatty acid composition of the algae oil comprises at least about 90% fatty acids of the types C16:1 and C18:1.

In further embodiments, the fraction comprising C16:1 and C18:1 fatty acids comprises at least about 60% C16:1 fatty acids. In further embodiments, the fraction comprising C16:1 and C18:1 fatty acids comprises at least about 70% C16:1 fatty acids. In further embodiments, the fraction comprising C16:1 and C18:1 fatty acids comprises at least about 80% C16:1 fatty acids. In further embodiments, the fraction comprising C16:1 and C18:1 fatty acids comprises at least about 90% C16:1 fatty acids.

In further embodiments, the fraction comprising C16:1 and C18:1 fatty acids comprises at least about 35% C18:1 fatty acids. In further embodiments, the fraction comprising C16:1 and C18:1 fatty acids comprises at least about 40% C18:1 fatty acids. In further embodiments, the fraction comprising C16:1 and C18:1 fatty acids comprises at least about 50% C18:1 fatty acids. In further embodiments, the fraction comprising C16:1 and C18:1 fatty acids comprises at least about 60% C18:1 fatty acids. In further embodiments, the fraction comprising C16:1 and C18:1 fatty acids comprises at least about 70% C18:1 fatty acids. In further embodiments, the fraction comprising C16:1 and C18:1 fatty acids comprises at least about 80% C18:1 fatty acids. In further embodiments, the fraction comprising C16:1 and C18:1 fatty acids comprises at least about 90% C18:1 fatty acids.

The composition rich in omega-7 fatty acids derived from algae may be used in a variety of products in fields such as, but not limited to, cosmetics, nutrition, medicine and pharmaceuticals. The products may include, but are not limited to, lipsticks, lip balm, skin makeup, nail varnish, makeup remover, hair loss prevention, hair treatment, hair color/dye protection, hair growth, dry skin treatment, skin lightening, dietary supplement, cholesterol treatment, skin rejuvenation, cardiovascular system treatment, nervous system treatment, human development, inflammation treatment, skin treatment, gastro-intestinal system treatment, respiratory system treatment, musculoskeletal system treatment, anti-biotics, beverage, food, food ingredient, feed and feed ingredient products. The products may take the form of topical and/or oral products, including consumable products. In some embodiments, the products take the form of rectal, nasal, transdermal, vaginal, parenteral, intramuscular, sub-cutaneous, inhalation, and insufflation administered products.

Algae comprising the composition rich in omega-7 fatty acids may also be used in a variety of products in fields such as, but not limited to, cosmetics, nutrition, medicine and pharmaceuticals. The products may include, but are not limited to, lipsticks, lip balm, skin makeup, nail varnish, makeup remover, hair loss prevention, hair treatment, hair color/dye protection, hair growth, dry skin treatment, skin lightening, dietary supplement, cholesterol treatment, skin rejuvenation, cardiovascular system treatment, nervous system treatment, human development, inflammation treatment, skin treatment, gastro-intestinal system treatment, respiratory system treatment, musculoskeletal system treatment, anti-biotics, beverage, food, food ingredient, feed and feed ingredient products. The products may take the form of topical and/or oral products, including consumable products. In some embodiments, the products take the form of rectal, nasal, transdermal, vaginal, parenteral, intramuscular, sub-cutaneous, inhalation, and insufflation administered products. Within the composition of a product, the algae may provide a fat soluble component, a dermatological active agent, an anti-inflammatory agent, a polyunsaturated fatty acid, a gelling agent, a calmative, a moisturizer, a polymer, an oil soluble plant extract, a thickening agent, an anti-seborrhoeic active agent, a water soluble heteropolysaccharide, a polysaccharide, a skin dye, an antioxidant, an anti-aging active agent, an agent for increasing glycosaminoglycan synthesis, an alcohol oxidase enzyme, a binder, and fibers. The omega-7 rich algae and the omega-7 rich composition may be used in products for both humans and non-human animals.

Additionally, the omega-7 rich algae and the omega-7 rich composition may also be used in medical applications such as, but not limited to: treating hyperglycemia, treating hyerptirglyceridemia, increasing insulin sensitivity, improving depatic lipid metabolism, preventing beta-cell apoptosis, reducing total and LDL cholesterol, improving circulating lipid profile, raising HLD cholesterol levels, lowering triglyceride levels, regulating cancerous and tumorous cells in the human body, protecting cells against cytoxicity, protecting cells against apoptosis, protecting cells against necrosis, lowering the risk of new-onset diabetes, and as a carrier for therapeutic agents in a biological system. In some embodiments, a pharmaceutical composition the omega-7 rich algae or the omega-7 rich composition may administered in forms such as, but not limited to: tablets, capsules, gels, slow releasers, patches, cachets, powder, granules, liquids, solutions, suspensions, emulsions, pastes, and coatings.

The omega-7 rich algae and the omega-7 rich composition may also be used in skin treatment applications such as, but not limited to: aiding cell rejuvenation, aiding healing, supporting cell regeneration, aiding in the healing of burns and wounds, reducing dermatitis, reducing eczema, aiding in protection from the harmful effects of the sun, increasing triglyceride concentration in the lipid barrier of the skin, and enhancing the protective nature of the stratum corneum. The omega-7 rich algae and the omega-7 rich composition may also be used in nutritional, food and feed applications such as, but not limited to: supplementing infant food and formulas to aid in the development of organs, eyes, skin, and hair; supplementing maternal food, and supplementing geriatric food.

Methods of Isolating Omega-7 Fatty Acids

Omega-7 fatty acids may be isolated from biomass sources using a variety of methods. Known methods of extracting and isolating fatty acids from algae include, but are not limited to: Bligh and Dyer's solvent extraction method; solvent extraction with a mixture of ionic liquids and methanol; hexane solvent extraction; ethanol solvent extraction; methanol solvent extraction; soxhlet extraction; supercritical fluid/CO2 extraction; ultrasonic/sonication; microwave irradiation; expression/expeller press; enzymatic extraction; osmotic shock; electromagnetic pulsing; bead milling; homogenization; mesoporous particles, and organic solvent (e.g., benzene, cyclohexane, hexane, acetone, chloroform) extraction. Any known method for extracting and isolating fatty acids algae may be used alone or in combination with one or more other known methods to obtain a composition enriched in omega-7 fatty acids from biomass for use as a product or in products.

While fatty acids may be extracted and isolated from biomass by a variety of methods, the extraction method used may affect the fatty acid composition recovered from algal biomass. Characteristics that the extraction method may vary include: concentration, volume, purity, and type of fatty acids recovered from the algal biomass. For example, hexane extraction has been shown to produce higher recovery rates than soxhlet extraction when used to extract fatty acids from algal biomass. Additionally, ionic liquid extraction has been shown to extract C18:1 fatty acids from algal biomass with some ionic liquids, but all ionic liquids. Also, using different solvent to water ratios in a solvent extraction method has been shown to affect the type of products extracted from algal biomass, including polar lipids and neutral lipids. The extracted products may be processed further using separation methods such as, but not limited to: distilling, decanting, and centrifuging; to further isolate and purify a fraction enriched in omega-7 fatty acids.

In one embodiment, the purity of the isolated omega 7 is greater than 50%, or preferably between a range of 70% and 99% and most preferably greater than 90%. In an alternate embodiment, more than one product streams are co-produced, each with a purity of omega 7 greater than 90%. In a different embodiment, there are three or more co-products, whereby one comprises a mixture rich in omega 7 while the other two or more co-product streams are lean in omega-7. In this inventive process, one of the co-product streams is used for fuel and/or for a high protein product.

The strain of algae that the fatty acids are being extracted from will also affect the fatty acid recovery. For example, hexane extraction has been shown to produce an algae oil recovery rate of 25.3% when used with *Scenedesmus dimorphus*, while hexane extraction has been shown to produce a lower algae oil recovery rate of 18.8% when used with *Chlorella protothecoides*. This variability in the algae oil extraction process emphasizes the impact that the selection of extraction method or methods for a specific algae strain has on the process efficiency and resulting fatty acid compositions or products.

Exemplary methods of and systems for isolation of palmitoleic acid from algal sources are disclosed. In one aspect of the invention, palmitoleic acid is isolated from an algal source. In some embodiments, an algal lipid extract comprising neutral lipids, carotenoids and chlorophyll is transesterified and subsequently distilled to produce a fraction rich in omega-7 acids. In further embodiments, this omega-7-rich fraction is then processed in a crystallization step to isolate at least one omega-7 product. In other embodiments, this omega 7 rich fraction may be further purified using various versions of chromatography such as the typical organic solvent chromatography, and supercritical fluid chromatography.

Figure 1:
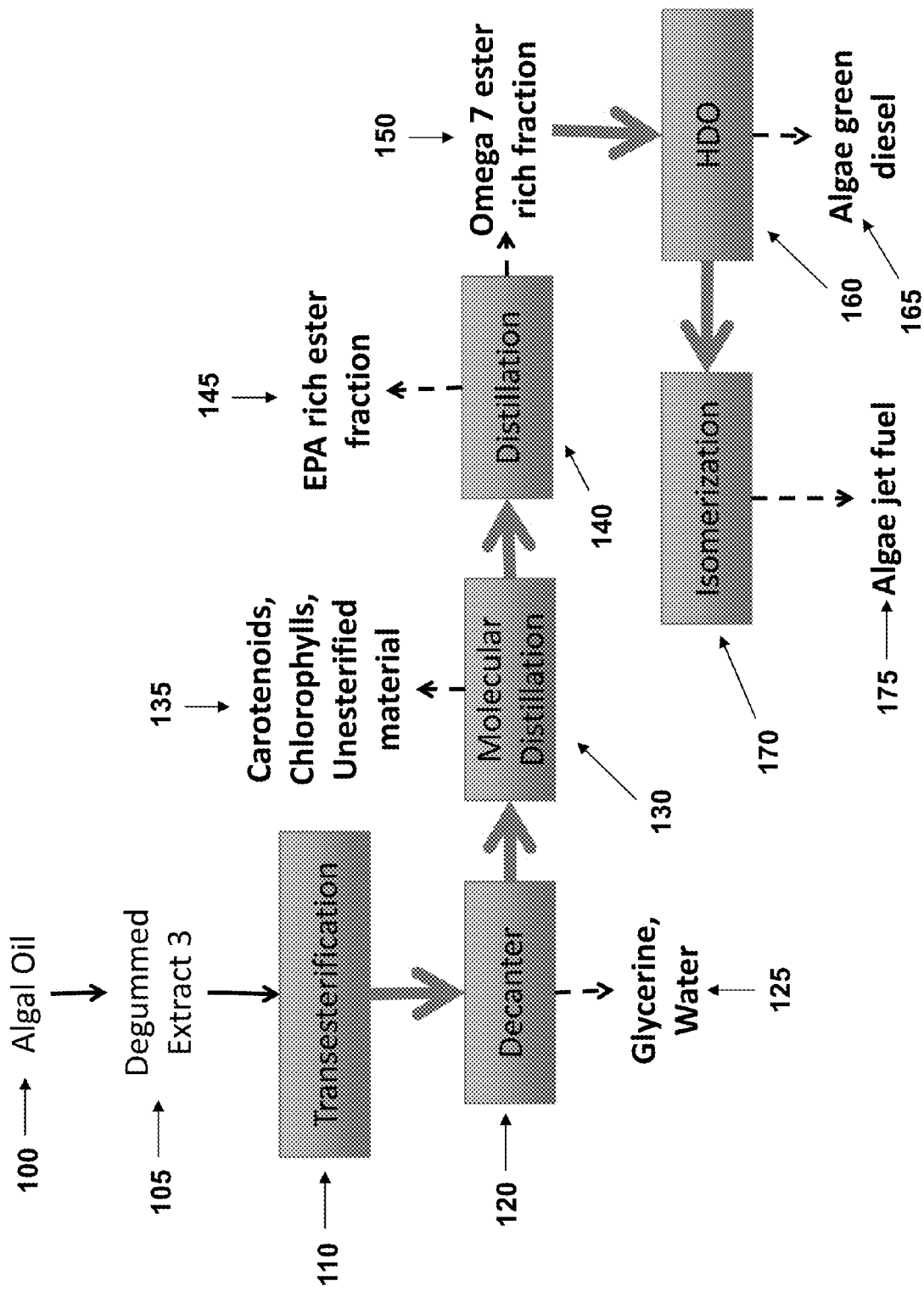
FIG. 1 is a flowchart of steps involved in method according to an exemplary embodiment of the present disclosure.

Referring now to FIG. 1, a flowchart provides an overview of the steps involved in exemplary embodiments of methods used in the isolation of palmitoleic acid from an algae-containing biomass. In a first step, Algal oil 100 is provided. Algal oil is generated by the steps of harvesting algal cells, removing water from the algal cells to yield a 10-25% solid biomass, using a solvent-based extraction on the biomass, and conducting a solid/liquid phase separation. In some embodiments, dewatering is accomplished using techniques including, but not limited to, dissolved air floatation, membrane filtration, flocculation, sedimentation, filter pressing, decantation or centrifugation. Dewatering is the removal of some most, or all of the water from a solid or semisolid substance. Dewatering can be carried out using any one of or a combination of any of the methods described herein, as well as by any other methods known to those skilled in the art. In some embodiments, solvent-based extraction is conducted with water-miscible slightly non-polar solvents (e.g., alcohols), in a multistage countercurrent solvent extraction process, segregating the fractions at each stage. This type of process can reduce both capital and operating expenses. In some embodiments, the biomass also undergoes acid and/or alkaline extraction to fractionate protein material. In some embodiments, separation is accomplished by filtration, decanting and/or centrifugation.

In a second step, Algal oil 100 is degummed to produce Degummed Algal oil 105. In some embodiments, degumming is a physical and/or chemical process of the oil 100 which results in removal of polar lipids (e.g., glycolipids and phospholipids) from the mixture. In some embodiments, degumming is accomplished by acid washing the neutral lipids to reduce the levels of metals and phospholipids in the neutral lipids. In some embodiments, a relatively dilute solution of phosphoric acid is added to the neutral lipids, and the mixture is heated and agitated. The precipitated phospholipids and metals are then separated from the remaining oil, for example, by centrifuge. A third step is transesterification 110, followed by decanter 120, which removes glycerine and water byproducts 125. Next, molecular distillation 130 is performed, which removes carotenoids, chlorophylls and unesterified material 135 from the mixture, which then undergoes further distillation 140 (which in some embodiments is non-molecular distillation), yielding an EPA (eicosapentaenoic acid) rich ester fraction 145 and the desired omega-7 ester rich fraction 150 (which in some embodiments in biodiesel). In the subsequent step, HDO (hydrodeoxygenation) 160 is performed, resulting in algae green diesel 165, while the desired material undergoes isomerization 170 to produce algae jet fuel 175.

Figure 2:
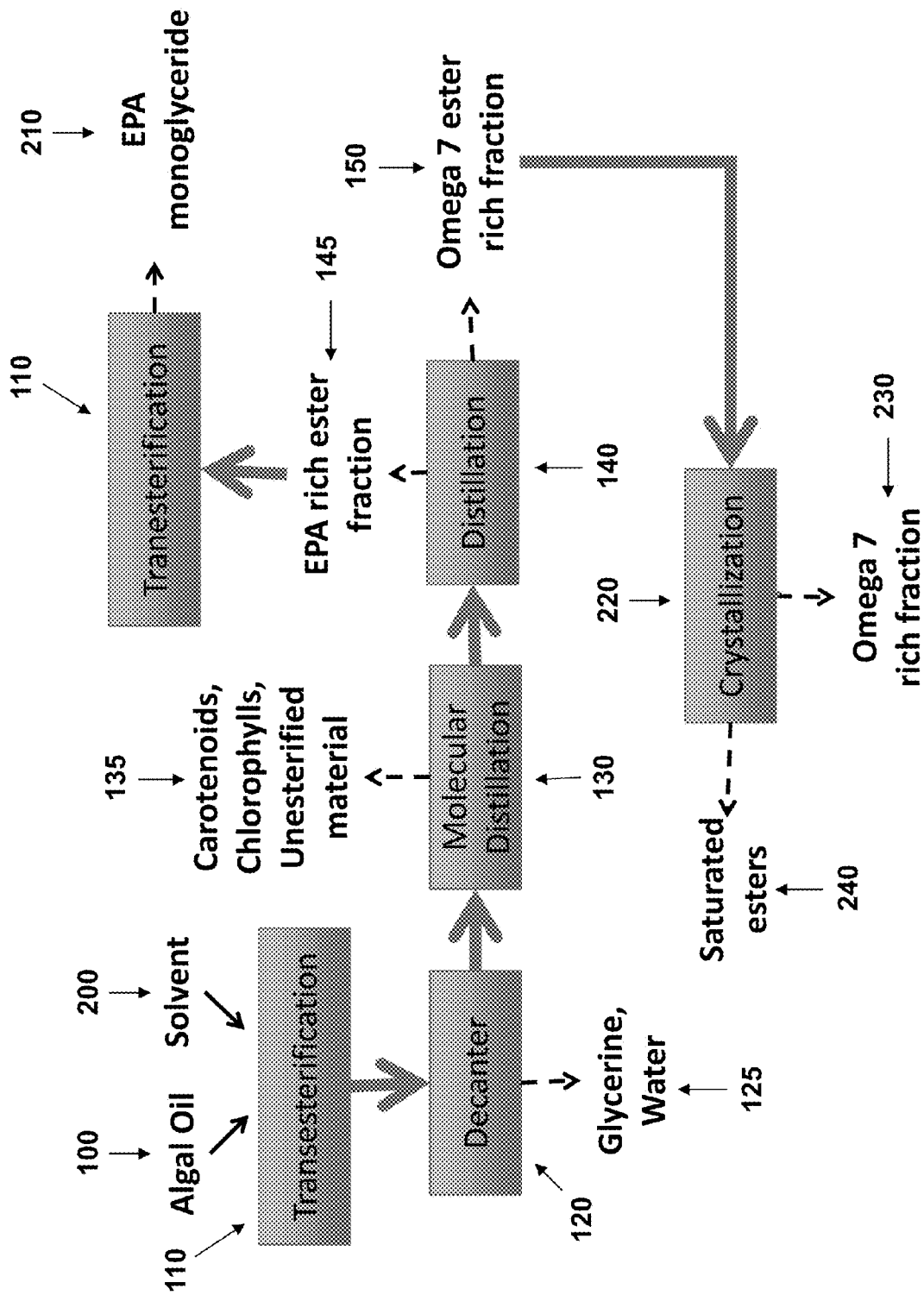
FIG. 2 is a flowchart of steps involved in a method according to an exemplary embodiment of the present disclosure.

Referring next to FIG. 2, a flowchart provides an overview of the steps involved in exemplary embodiments of methods used in the isolation of palmitoleic acid from an algae-containing biomass. In a first step, Algal oil 100 and solvent 200 are combined and undergo transesterification 110. After decanter 120 removes glycerine and water 125, the mixture undergoes molecular distillation 130 to remove carotenoids, chlorophylls and unesterified material 135. Subsequently, distillation 140 is performed (which in some embodiments is non-molecular distillation) which produces an EPA rich ester fraction 145 and omega-7 ester rich fractions 150. Next, EPA rich ester fraction 145 undergoes further transesterification 110 to produce EPA monoglyceride 210. Meanwhile, omega-7 ester rich fraction 150 undergoes crystallization 220 to produce an omega-7 rich fraction 230 and saturated esters 240 (which can be biodiesel). Crystallization (also known as cold fractionation) is purification of a mixture of compounds in a liquid state wherein materials are separate based on disparate melting points. In some embodiments, a liquid comprises an omega-3 faction (comprising EPA), an omega-7 fraction (comprising C18:1n9 oleic and C16:1n7 palmitoleic acids) and a biofuel or biochemical fraction (comprising C16 palmitic and C18 stearic acids). In some embodiments, distillation 140 separates EPA (omega-3) rich ester fraction 145 from omega-7 ester rich fraction 150, which also comprises saturated esters 240. Subsequently, crystallization 220 is conducted to separate omega-7 rich fraction 230 from saturated biofuel esters 240.

An illustrative apparatus for crystallization or cold fractionation 220 is a vessel to contain a liquid mixture, wherein a heat exchanger coil is suspended in the liquid. The liquid mixture is slowly stirred while a chilling liquid is pumped through the coil to achieve a desired temperature gradient in the liquid. The higher melting point material begins to collect on the surface of the coil and/or aggregate in lumps in the liquid mixture. The temperature of the coil and the resulting gradient is a function of the melting points of the compounds in the mixture.

Figure 3:
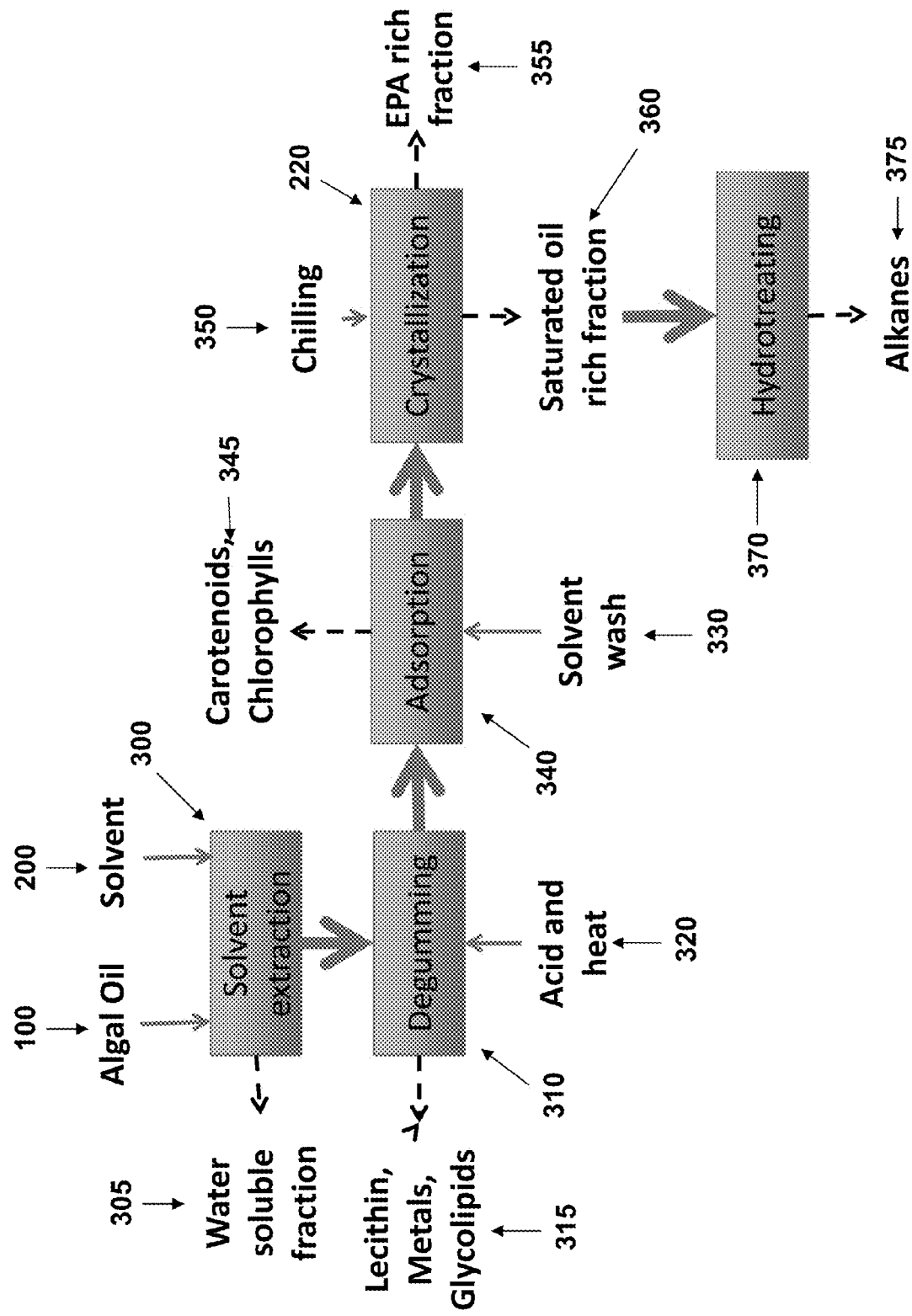
FIG. 3 is a flowchart of steps involved in a method according to an exemplary embodiment of the present disclosure.

Referring next to FIG. 3, a flowchart provides an overview of the steps involved in exemplary embodiments of methods used in the isolation of palmitoleic acid from an algae-containing biomass. In a first step, Algal oil 100 and solvent 200 are combined and undergo solvent extraction 300, removing water soluble fraction 305. The desired material then undergoes degumming 310 with the addition of acid and heat 320, which removes lecithin, metals and glycolipids 315 from the desired mixture. Next, adsorption 340 with solvent wash 330 removes carotenoids and chlorophylls 245, followed by crystallization or cold fractionation 220 with chilling 350, which provides an EPA rich fraction 355 and a saturated oil rich fraction 360, which can be used for fuel. The saturated oil rich fraction 360 then undergoes hydrotreating 370 to produce alkanes 375.

Figure 5:
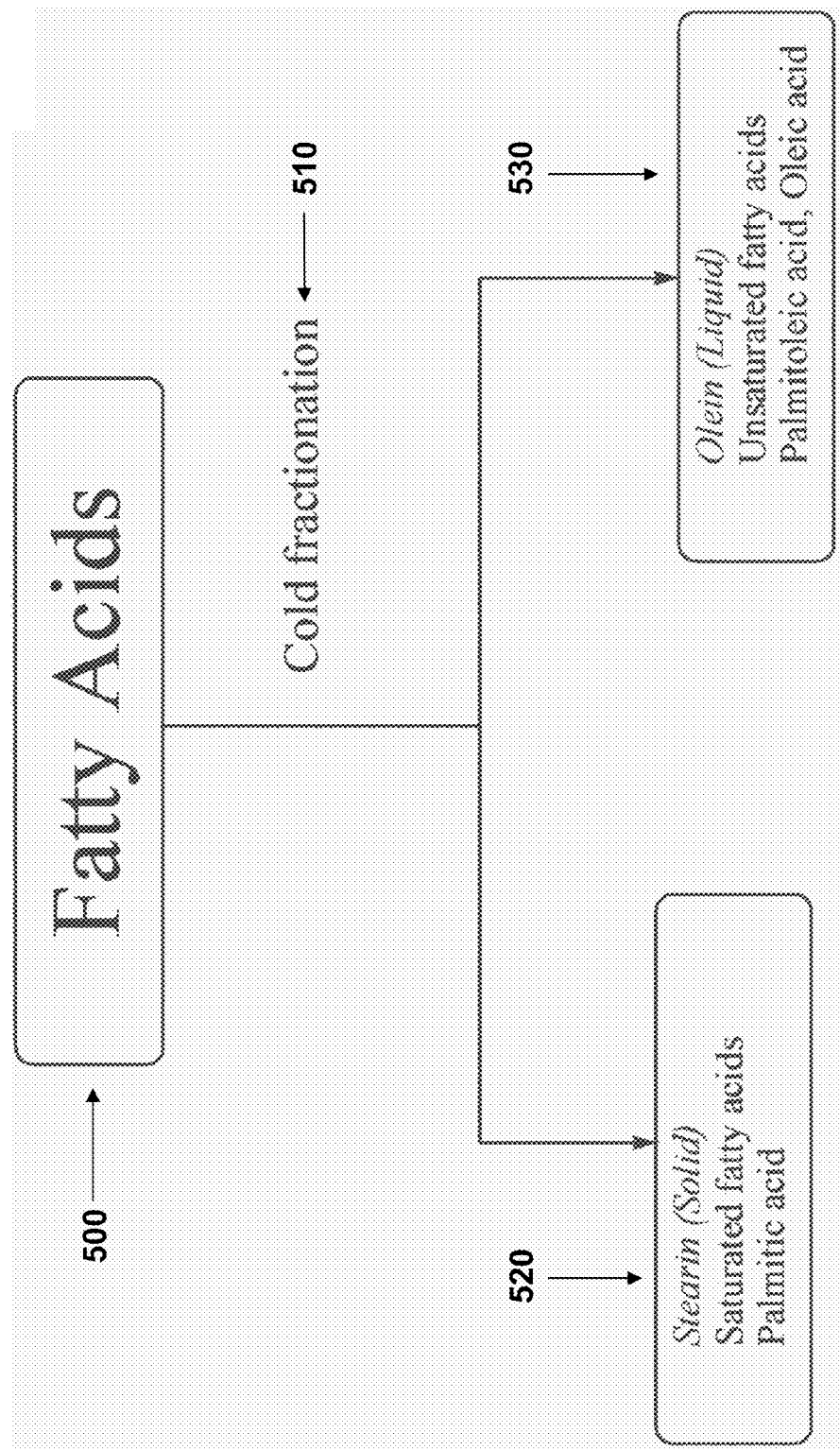
FIG. 5 is a flowchart of steps involved in a method according to an exemplary embodiment of the present disclosure.

Referring to FIG. 5, a flow chart provides an overview of the steps involved in exemplary embodiments of methods used in the isolation of palmitoleic acid from an algae-containing biomass. In a first step, fatty acids 500 are provided. Next, cold fractionation or crystallization 510 is conducted which separates the mixture into a solid phase 520, which comprises saturated fatty acids such as palmitic acid and a liquid phase 530 which comprises unsaturated fatty acids such as palmitoleic acid and oleic acid.

Figure 6:
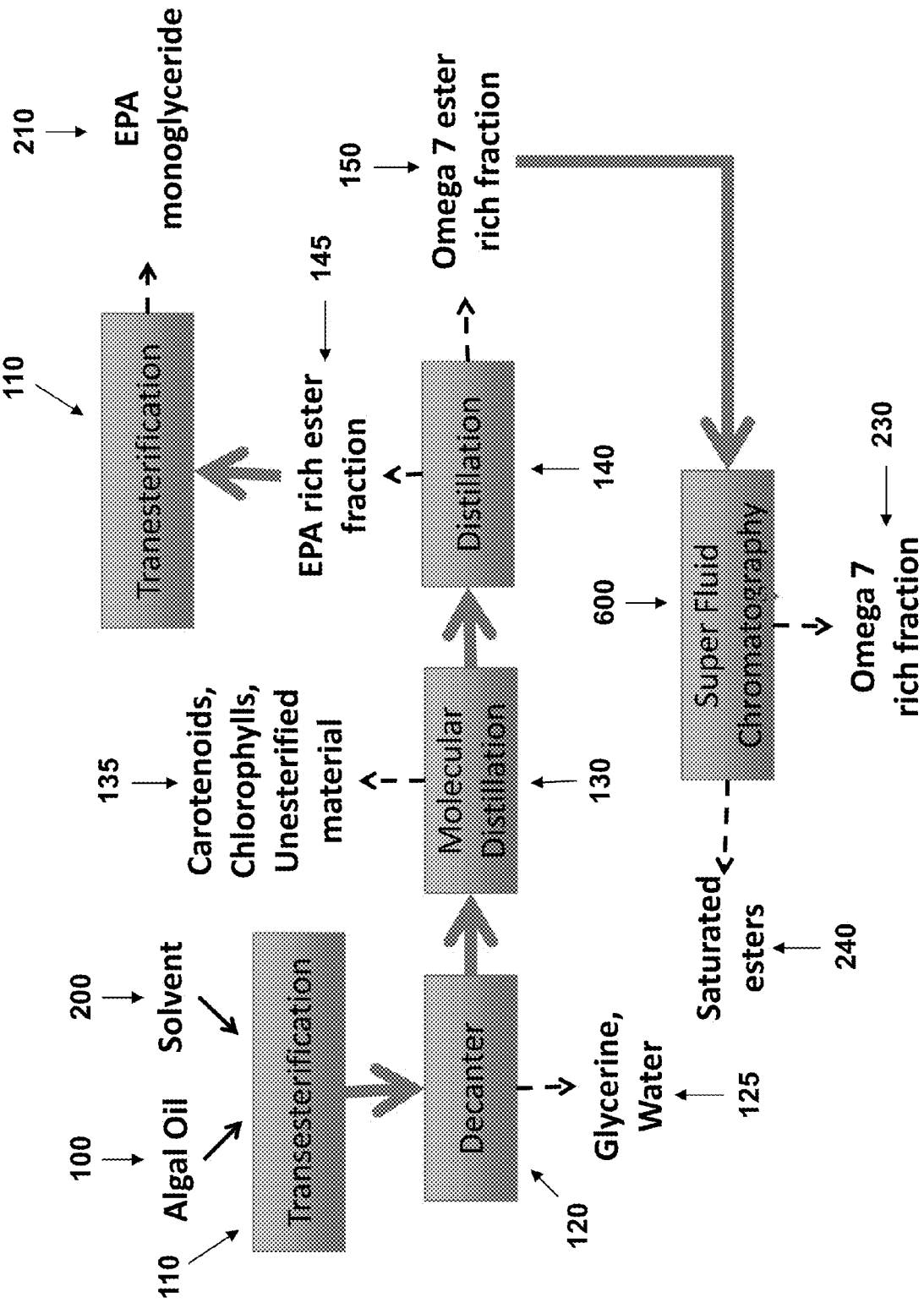
FIG. 6 is a flow chart of steps involved in a method according to an exemplary embodiment of the present disclosure.

Referring next to FIG. 6, a flowchart provides an overview of the steps involved in exemplary embodiments of methods used in the isolation of palmitoleic acid from an algae-containing biomass. In a first step, Algal oil 100 and solvent 200 are combined and undergo transesterification 110. After decanter 120 removes glycerine and water 125, the mixture undergoes molecular distillation 130 to remove carotenoids, chlorophylls and unesterified material 135. Subsequently, distillation 140 is performed (which in some embodiments is non-molecular distillation) which produces an EPA rich ester fraction 145 and omega-7 ester rich fractions 150. Next, EPA rich ester fraction 145 undergoes further transesterification 110 to produce EPA monoglyceride 210. Meanwhile, omega-7 ester rich fraction 150 undergoes supercritical fluid chromatography 600 to produce an omega-7 rich fraction 230 and saturated esters 240 (which can be biodiesel). Supercritical fluid chromatography (also known as SFC) is purification of a mixture of compounds in a liquid state wherein materials are separated based on selectivity of a packed solid bed adsorbent to saturated and unsaturated esters. In some embodiments, a liquid comprises an omega-3 faction (comprising EPA), an omega-7 fraction (comprising C18:1n9 oleic and C16:1n7 palmitoleic acids) and a biofuel or biochemical fraction (comprising C16 palmitic and C18 stearic acids). In some embodiments, distillation 140 separates EPA (omega-3) rich ester fraction 145 from omega-7 ester rich fraction 150, which also comprises saturated esters 240. Subsequently, SFC 600 is conducted to separate omega-7 rich fraction 230 from saturated biofuel esters 240.

An illustrative apparatus for supercritical fluid chromatography 600 is a solid packed column to contain the adsorbent such as zeolite or modified silica, wherein the ester mixture is pumped onto the column for complete adsorption followed by a sequential elution of the saturated and unsaturated esters using supercritical CO2 with or without a modifier such as ethanol. This method can result in very high purities in the order of 99%.

Example 1

An experiment was performed with *Nannochloropsis* biomass (cultured from strain 202.0, obtained from Arizona State University, Laboratory for Algae Research and Biotechnology, ATCC Deposit Number PTA-11048), was harvested and dewatered until the algae comprised about 35% w/w and then finally frozen at −40 C until the extraction. A pre-weighed amount of wet algal biomass (1000 grams) and 1000 mL of ethanol solvent were added into a three-neck flask equipped with condenser, mechanical stirring and a thermocouple. The mixture was stirred at 700 rpm and heated to 70 C. The system was held at temperature (70 C) for 1 hour. This was followed by centrifuging to decanting the extract 1. The residual extracted solids were re-extracted with 1000 mL ethanol and the process was repeated to obtain extract 2. The residual extracted solids were re-extracted with 1000 mL ethanol and the process was repeated three times to obtain algal oil. The algal oil was evaporated to concentrate the lipids. These lipids were degummed using the citric acid degumming process. A 50% (w/v) aqueous solution of citric acid prepared. The lipids were heated to 70 C under rapid stirring and the aqueous citric acid mixture (1% by weight of oil) was added to the lipids. The mixture was maintained at temperature for 1 hour and centrifuged to separate the phospholipids and glycolipids. The oil was then transesterified using (0.5% by weight of oil) sodium ethoxide dissolved in ethanol (30% weight of oil) at 70 C for 3 hours. The mixture was washed by adding equal amounts of water and hexane with low agitation. This mixture was centrifuged to separate the three layers. The top layer consisted of the ethyl esters dissolved in hexane; the middle layer was an emulsion resulting from agitation, etc. and was further washed one more time; the lower layer was the aqueous layer with glycerine and hydroxide resulting from the reaction. The ethyl esters were distilled under high vacuum at 70 C to separate the omega 7 ester rich fraction. The bottoms consisted of the carotenoids, omega 3 esters rich fraction.

Figure 7:
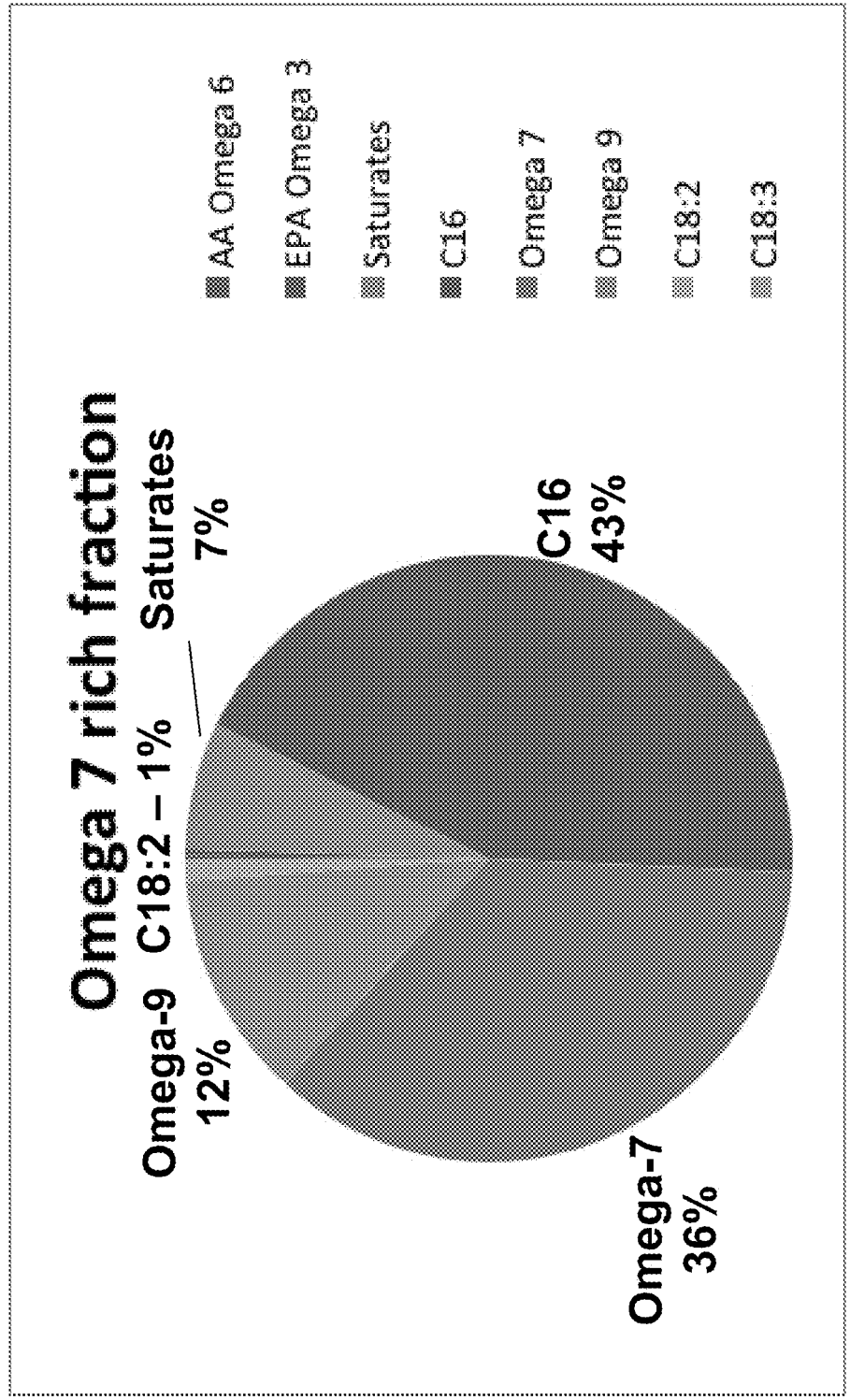
FIG. 7 is a pie chart of the relative amounts of substances present in an exemplary mixture of an omega 7 rich fraction isolated from algae.
Figure 8:
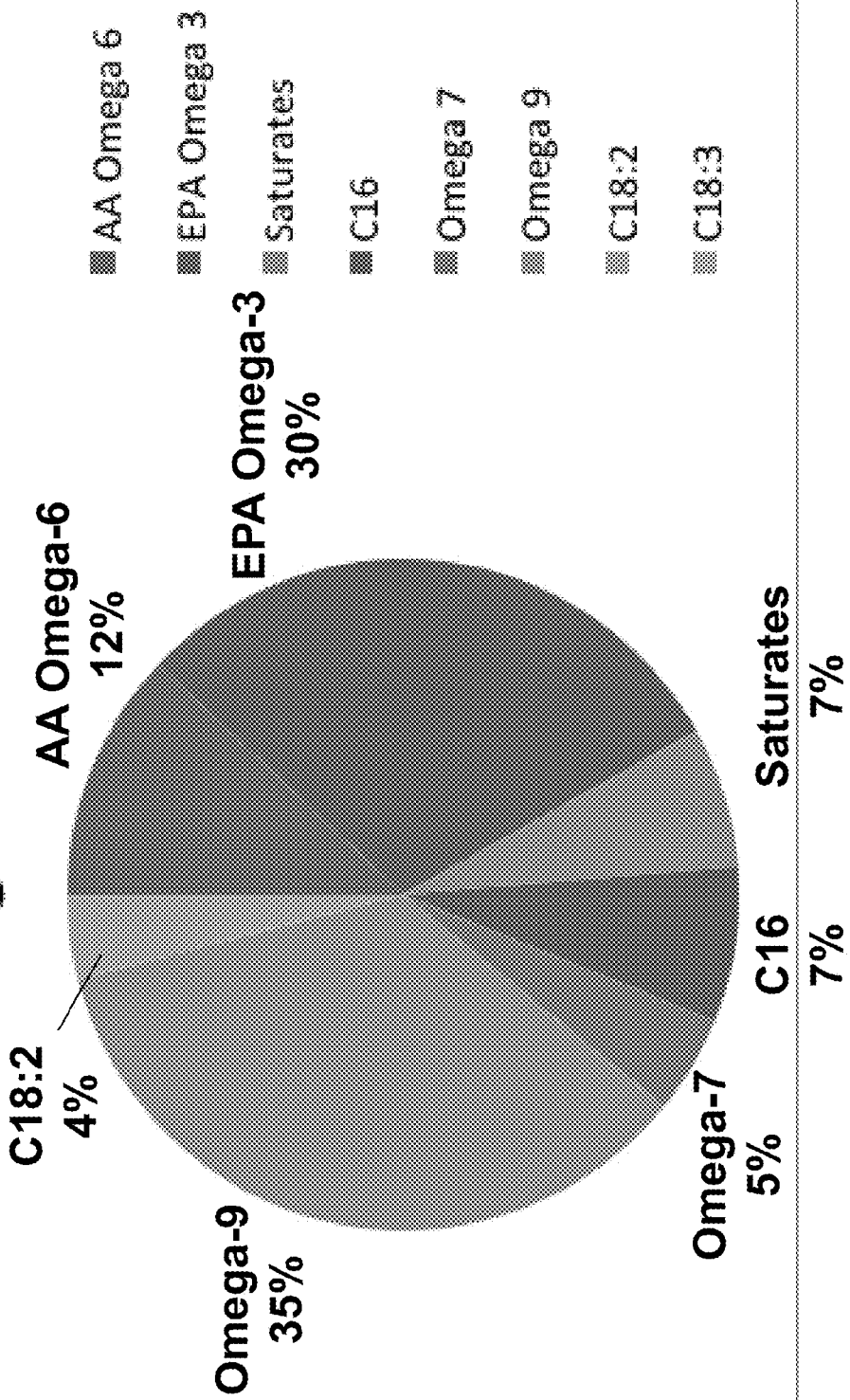
FIG. 8 is a pie chart of the relative amounts of substances present in an exemplary mixture of an omega 3 rich fraction isolated from algae.

FIGS. 7 and 8 display the composition of omega7 rich and omega 3 rich fractions obtained from the experiment using *Nannochloropsis* described in Example 1. FIG. 7 shows a pie chart of an exemplary composition of an omega 7 rich fraction isolated from *Nannochloropsis* in Example 1 comprising: about 43% C16 fatty acids, about 36% omega 7 fatty acids, about 12% omega 9 fatty acids, about 7% saturates, and about 1% C18:2 fatty acids. FIG. 8 shows a pie chart of an exemplary composition of an omega 3 rich fraction isolated from *Nannochloropsis* in Example 1 comprising: about 7% C16 fatty acids, about 5% omega 7 fatty acids, about 35% omega 9 fatty acids, about 7% saturates, about 4% C18:2 fatty acids, about 12% AA Omega 6 fatty acids, and about 30% EPA omega 3 fatty acids.

Example 2

In a prophetic example, the use of intermittent light with a defined high intensity light greater than about 500 micromoles per meter-squared per second is followed by a dark cycle of equal or longer time duration produces a higher content of omega-7 than a process without a light dark cycle. The light cycle may comprise predominately white light. The dark cycle may be predominately devoid of light. The light intensity is preferably for a short time duration, from about 1 millisecond to 10 seconds, then followed by a dark cycle of equal or greater time duration. In an alternate embodiment, the intensity of the light input is greater than about 1000 or 1500 micromoles per meter squared per second and the time duration is from about 1 millisecond to 10 seconds. In an additional embodiment, the light input may supplied by LED or micro-LED lights to control the intensity and duration of the light input. Further, a specific color of light may be added, e.g. red light or blue light, for one or more of the light cycles during a 24 hour period. In one embodiment, the duration time for the red light cycle is longer than the time duration for the other white light cycles.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method of isolating an omega-7 fatty acid ester from algal biomass, comprising the steps of:
    (a) Extracting oil from algal biomass comprising C16:1 fatty acids;
    (b) Transesterifying the extracted oil to generate a first algal extract mixture;
    (c) Decanting the first algal extract mixture to separate a second algal extract fraction and a fraction comprising glycerine and water;
    (d) A first distilling of the second algal extract fraction to separate a third algal extract fraction and a fraction comprising carotenoids, chlorophylls, and unesterified material;
    (e) A second distilling of the third algal extract fraction to separate a fraction rich in omega-7 esters and a fraction rich in eicosapentaenoic acid (EPA) esters; and
    (f) Isolating the fraction rich in omega-7 esters from the fraction rich in EPA esters.

2. The method of claim 1, further comprising: degumming the extracted oil.

3. The method of claim 1, further comprising: hydrodeoxygenating the fraction rich in omega-7 esters to generate an algae green diesel fraction.

4. The method of claim 3, further comprising: isomerizing the algae green diesel fraction to generate an algae jet fuel fraction.

5. The method of claim 1, wherein the first distilling step is a molecular distillation.

6. A method of isolating an omega-7 fatty acid ester from algal biomass, comprising the steps of:
    (a) Extracting oil from algal biomass comprising C16:1 fatty acids;
    (b) Adding a solvent to the extracted oil to generate a first algal extract mixture;
    (c) Transesterifying the first algal extract mixture to generate a second algal extract mixture;
    (d) Decanting the second algal extract mixture to separate a third algal extract fraction and a fraction comprising glycerine and water;
    (e) A first distilling of the third algal extract fraction to separate a fourth algal extract fraction and a fraction comprising carotenoids, chlorophylls, and unesterified material;
    (f) A second distilling of the fourth algal extract fraction to separate a first fraction rich in omega-7 esters and a fraction rich in eicosapentaenoic acid (EPA) esters; and
    (g) Isolating the first fraction rich in omega-7 esters from the fraction rich in EPA esters.

7. The method of claim 6, further comprising:
    (a) Crystallizing the first fraction rich in omega-7 esters to separate a second fraction rich in omega-7 and a fraction rich in saturated biodiesel esters.

8. The method of claim 6, further comprising:
    (a) Separating the first fraction rich in omega-7 esters using supercritical fluid chromatography into a second fraction rich in omega-7 and a fraction rich in saturated biodiesel esters.

9. The method of claim 6, further comprising:
    (a) Transesterifying the fraction rich in EPA esters to generate EPA monoglyceride.

10. The method of claim 6, wherein the first distilling step is a molecular distillation.

11. A method of producing alkanes from an algal oil, comprising the steps of:
   (a) Extracting oil from algal biomass;
   (b) Mixing the extracted oil with a solvent and heating in a solvent extraction process to generate a first algal extract fraction and a water soluble fraction;
   (c) Separating the first algal extract fraction and the water soluble fraction;
   (d) Degumming the first algal extract fraction with acid and heat to generate a second algal extract fraction and a fraction comprising lecithin, metals and glycolipids;
   (e) Separating the second algal extract fraction and the fraction comprising lecithin, metals and glycolipids;
   (f) Adsorption of the second algal extract fraction with a solvent wash to generate a third algal extract fraction and a fraction comprising carotenoids and chlorophylls;
   (g) Separating the third algal extract fraction and the fraction comprising carotenoids and chlorophylls;
   (h) Crystallizing the third algal extract fraction with chilling to separate a fraction rich in EPA and a fraction rich in saturated oils; and
   (i) Hydrotreating the fraction rich in saturated oils to generate alkanes.

* * * * *